United States Patent [19]
Abe et al.

[11] Patent Number: 5,456,255
[45] Date of Patent: Oct. 10, 1995

[54] ULTRASONIC DIAGNOSIS APPARATUS

[75] Inventors: Yasuhiko Abe, Ootawara; Takeshi Sato, Tochigi; Makoto Hirama, Ootawara, all of Japan

[73] Assignee: Kabushiki Kaisha Toshiba, Kawasaki, Japan

[21] Appl. No.: 272,587

[22] Filed: Jul. 11, 1994

[30] Foreign Application Priority Data

Jul. 12, 1993 [JP] Japan ................................. 5-171333

[51] Int. Cl.$^6$ ........................................... A61B 8/00
[52] U.S. Cl. .............................. 128/660.07; 128/660.05
[58] Field of Search ........................ 128/660.07, 660.05, 128/660.06, 661.07, 661.08, 661.09, 661.1, 661.04; 364/413.25

[56] References Cited

U.S. PATENT DOCUMENTS

| | | | |
|---|---|---|---|
| 4,771,470 | 9/1988 | Geiser et al. ...................... | 128/661.04 |
| 4,890,624 | 1/1990 | Ganguly et al. .................... | 128/661.07 |
| 5,241,473 | 8/1993 | Ishihara et al. ..................... | 364/413.25 |

Primary Examiner—George Manuel
Attorney, Agent, or Firm—Finnegan, Henderson, Farabow, Garrett & Dunner

[57] ABSTRACT

There is disclosed an ultrasonic diagnosis apparatus comprising a transmission/reception unit, a signal processing unit, a conversion unit, and a display unit. The transmission/reception unit transmits/receives ultrasonic waves to/from an object to be examined, thereby obtaining ultrasonic reception signals. The signal processing unit executes signal processing of the ultrasonic reception signals to obtain ultrasonic images. The conversion unit converts an ultrasonic image having a predetermined dynamic image obtained from the object to be examined to which a contrast medium is injected into an ultrasonic image having a dynamic range corresponding to that of the display unit. The display unit displays the ultrasonic image obtained by the conversion unit.

43 Claims, 16 Drawing Sheets

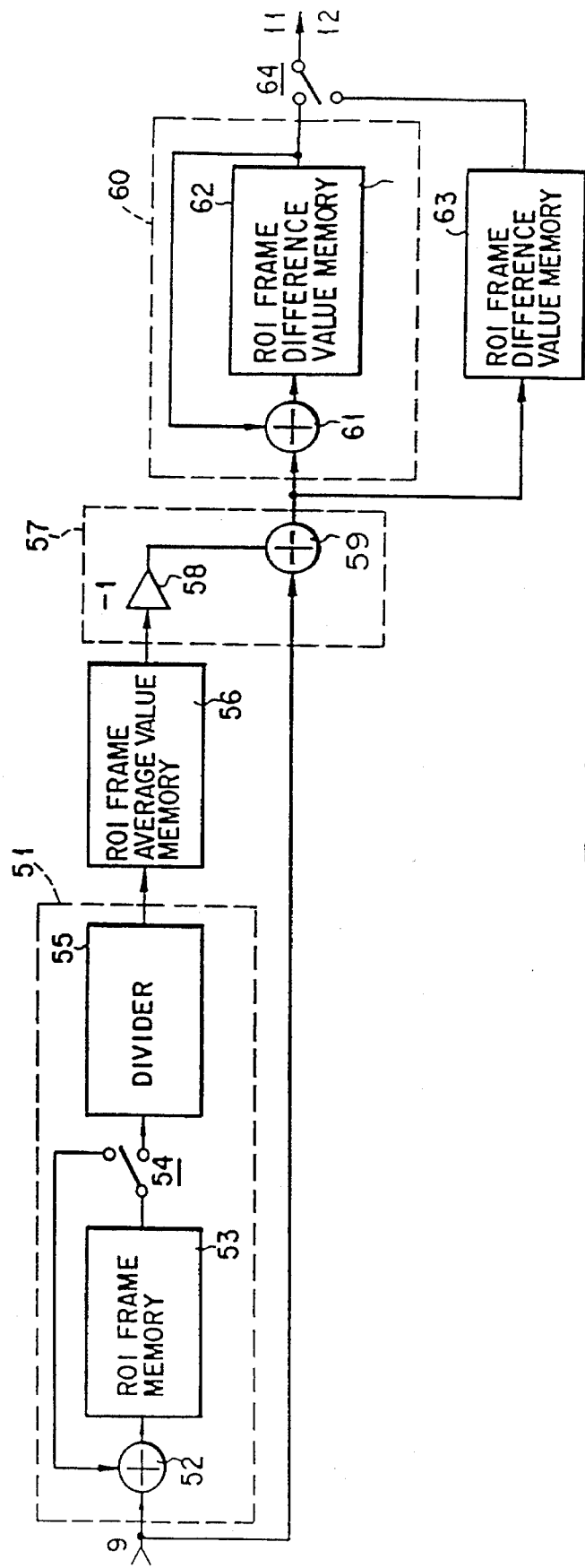
F I G. 7

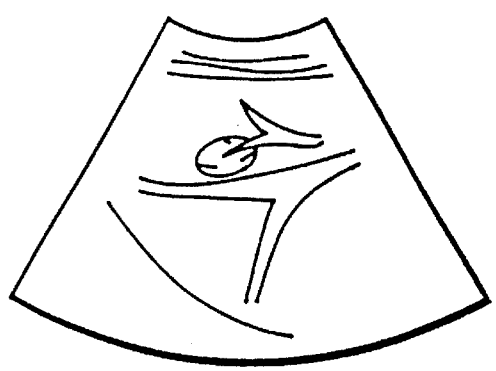
F I G 9A
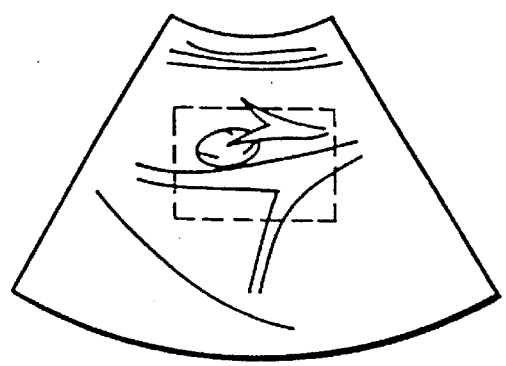
F I G 9B
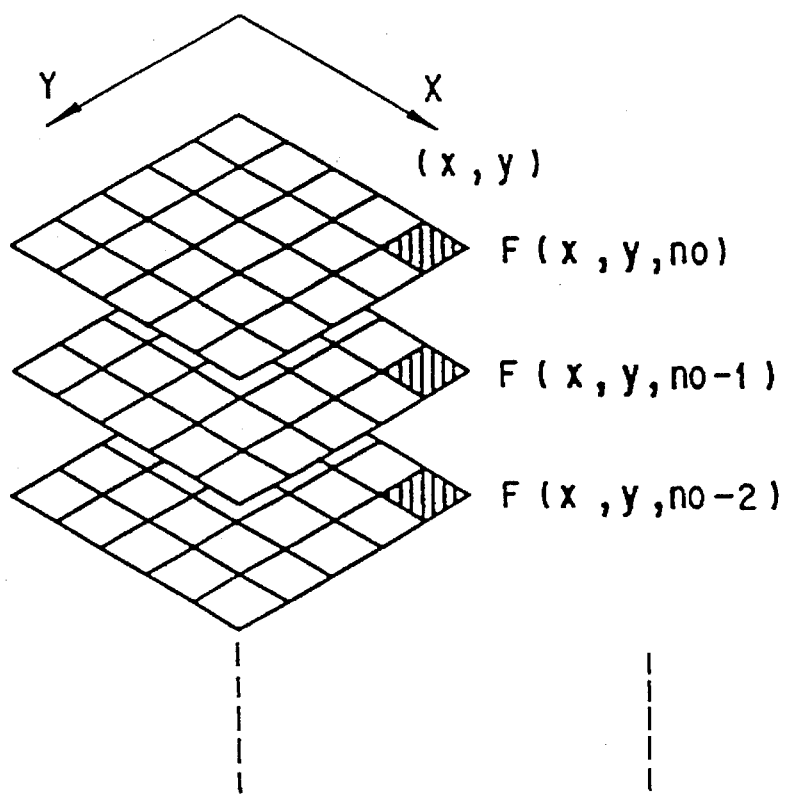
F I G. 10

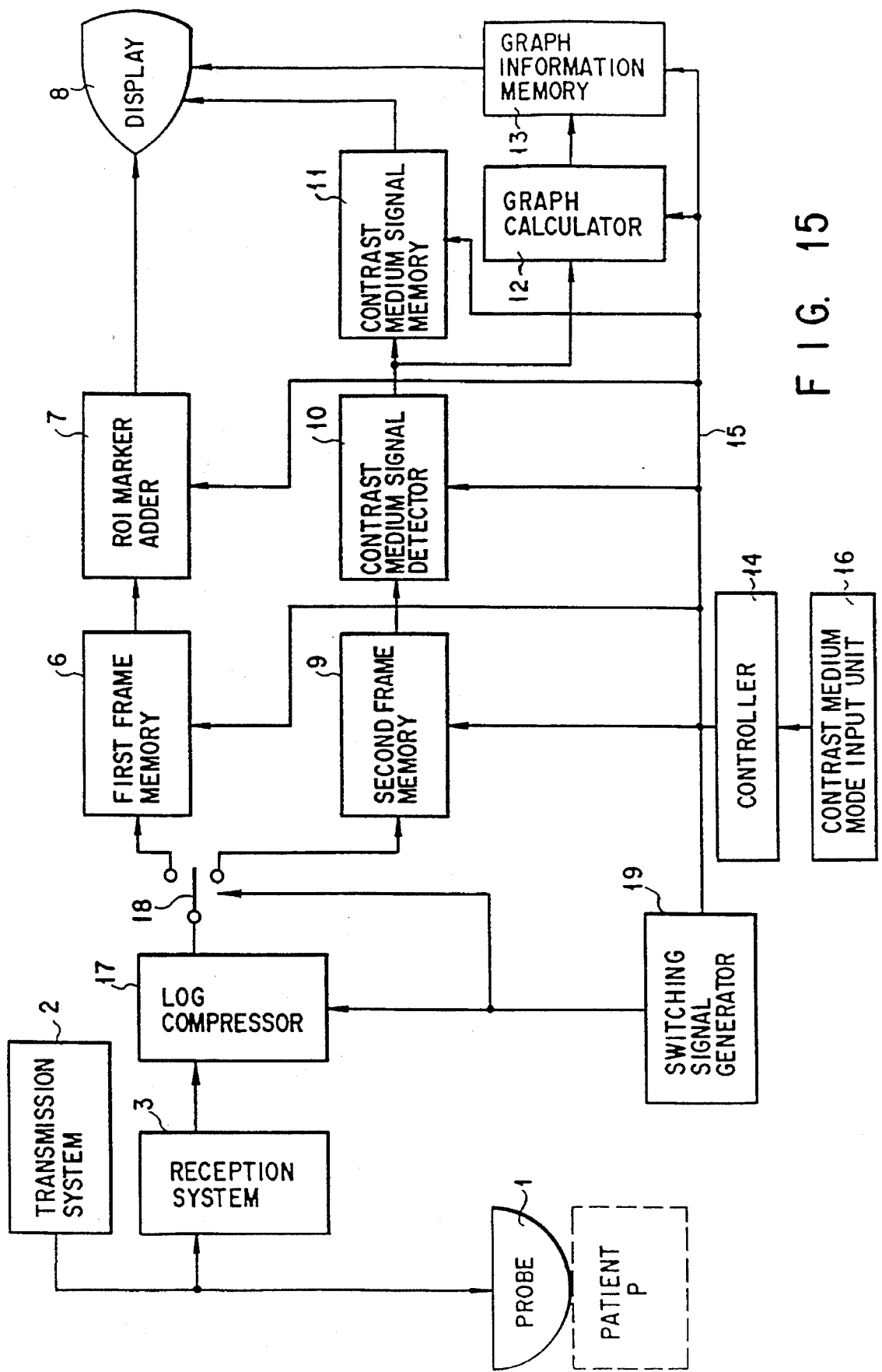
F I G. 15

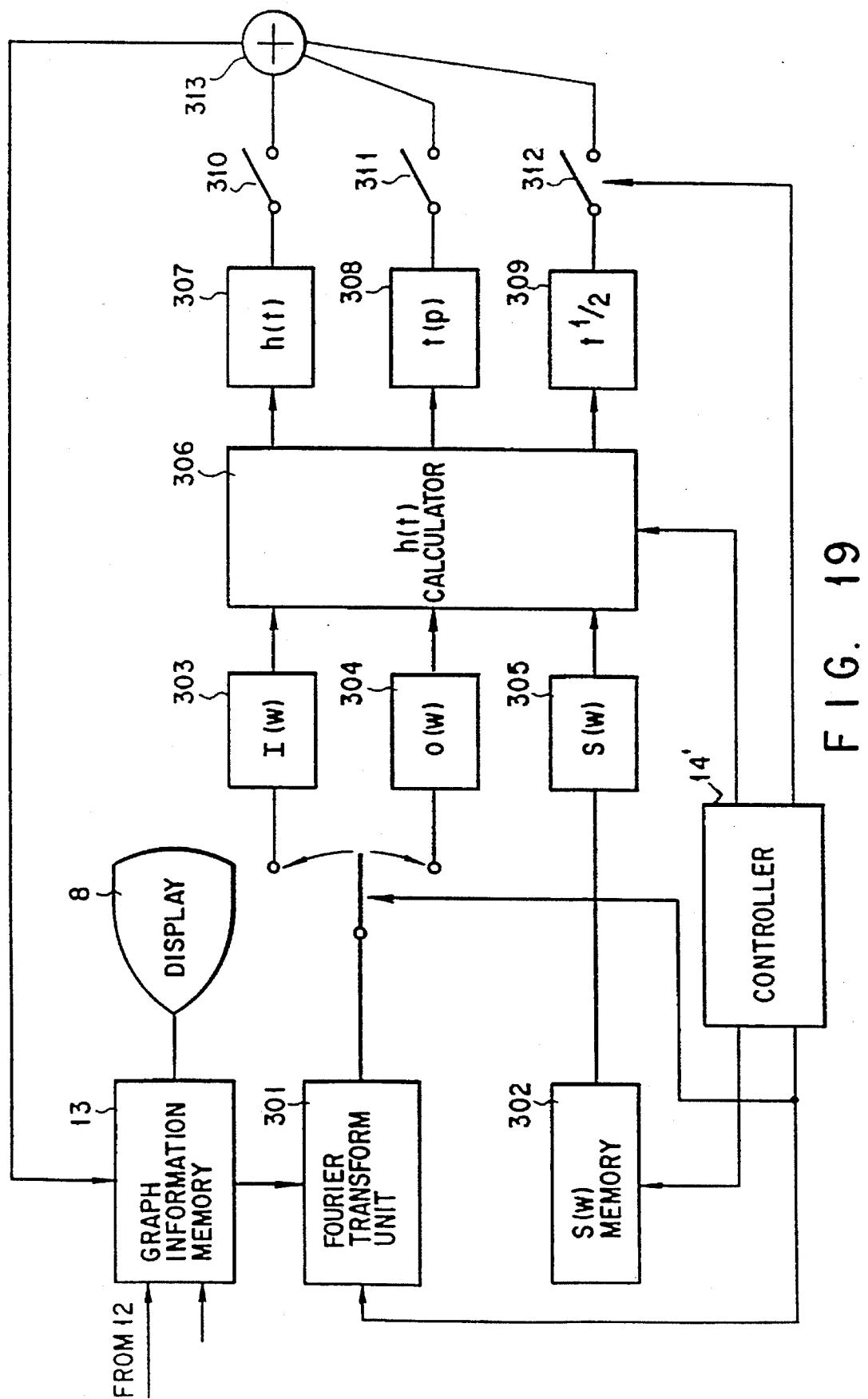
F I G. 19

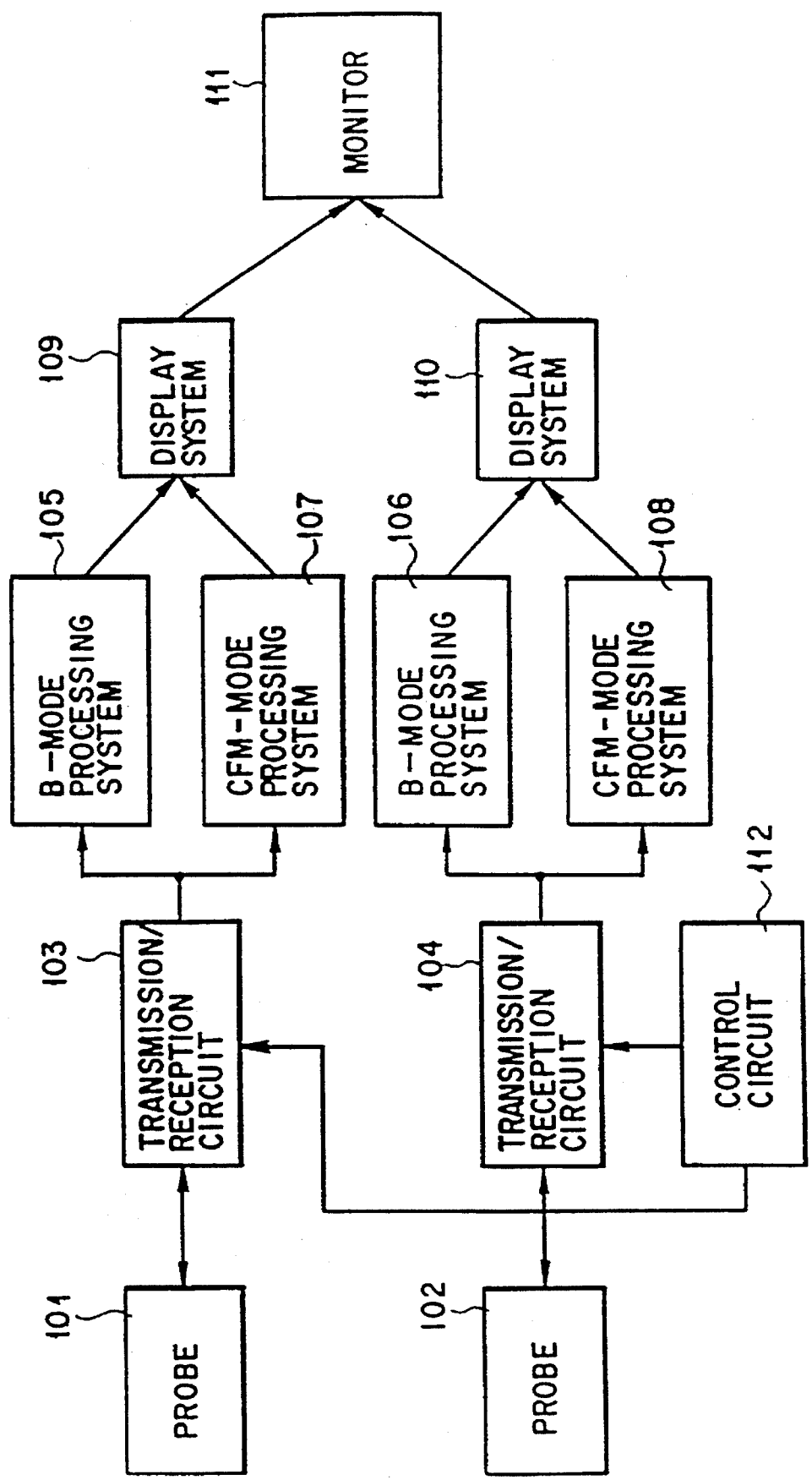
F I G. 21

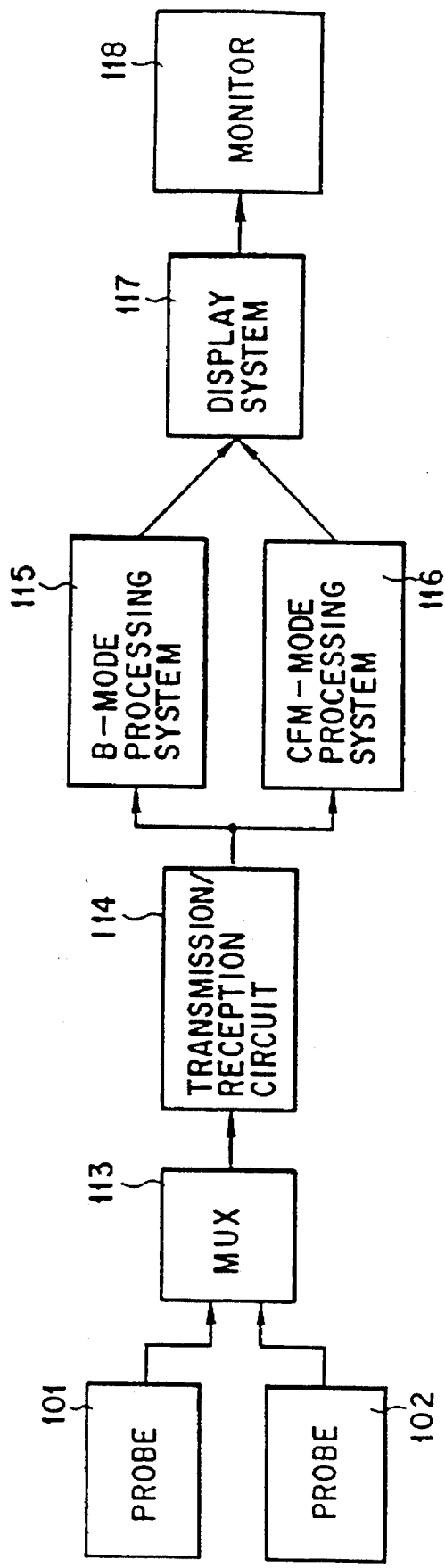
F I G. 22

ULTRASONIC DIAGNOSIS APPARATUS

BACKGROUND OF THE INVENTION

1. Field of the Invention

The present invention relates to an ultrasonic diagnosis apparatus which is applied to a diagnosis using an ultrasonic contrast medium.

2. Description of the Related Art

An ultrasonic diagnosis apparatus radiates ultrasonic pulses into a living body, receives waves reflected by a boundary surface between tissues having different specific acoustic impedances (products of the densities of the two media and the sonic speed), and acquires an image by processing the received waves. The ultrasonic diagnosis apparatus does not cause an exposure trouble unlike in an X-ray diagnosis method, and is a clinically effective apparatus. In addition, along with the advance of various kinds of techniques such as an electron scanning technique, real-time performance has been improved, and moving object measurement has become easier.

In recent years, as the development of an ultrasonic contrast medium progresses, expectations for a close blood-flow diagnosis equivalent to X-ray angiography have been keen. The ultrasonic contrast medium has a clearly different nature in a reception signal from a living body and its intensity. With this medium, since a portion into which an ultrasonic contrast medium flows has a different luminance or gradation level from that of other portions on a B-mode image, an observer can observe the flow-in state of the ultrasonic contrast medium.

visual observation of the flow-in state of the ultrasonic contrast medium can only provide very low accuracy. In order to improve diagnostic accuracy, various kinds of information such as a change, over time, in flow-in/out amount of a contrast medium in/from a region of interest, its rise time, and the like are required. Conventional ultrasonic diagnosis apparatuses cannot provide such kinds of information. For this reason, an observer measures the total density in a region of interest in units of frames, summarizes the measurement results in a graph, and uses the graph in diagnosis. As described above, in order to acquire various kinds of information, an observer is required to perform troublesome and time-consuming operations. In addition, such information cannot be obtained in real time. Furthermore, since a reception signal includes a living body component and a contrast medium component, the contrast medium component must be extracted from the reception signal in order to accurately measure the flow-in/out amount of the contrast medium in/from a region of interest. However, ultrasonic waves are influenced more easily by motions of a living body portion than X-rays, and their intensity is unstable over time even for a living body component of the same living body portion. For this reason, it is difficult to accurately extract the contrast medium component from the reception signal.

The dynamic range of a normal ultrasonic diagnosis apparatus is set to be an expected intensity width of a reception signal from living body tissues in order to increase contrast. For this reason, since the contrast medium component in the reception signal has a clearly different intensity from that of a reception signal from a living body, it may be saturated beyond the upper limit of the dynamic range. For this reason, image formation is often disabled.

Furthermore, it is effective to simultaneously observe two separate portions, e.g., the carotid artery and an internal vein in acquisition of the flow-in state of the contrast medium. For this reason, conventionally, two ultrasonic diagnosis apparatuses are used. However, beat noise components are generated in acquired images of each apparatus due to the influence of ultrasonic waves of the other apparatus. In addition, since the two apparatuses independently generate images, they have different standard signal levels due to differences of the electric/ultrasonic conversion characteristics of their probes, the gain characteristics of preamplifiers, and the like, and hence, the images acquired by the two apparatuses cannot be compared with each other.

SUMMARY OF THE INVENTION

It is an object of the present invention to provide an ultrasonic diagnosis apparatus which can prevent a contrast medium component of a reception signal from being saturated beyond the upper limit of the dynamic range.

It is another object of the present invention to provide an ultrasonic diagnosis apparatus which can provide various kinds of information such as a change, over time, in flow-in/out amount of a contrast medium in/from a region of interest in real time.

It is still another object of the present invention to provide an ultrasonic diagnosis apparatus which allows acquisition of images of two separate portions in real time while suppressing generation of beat noise components in each image due to the influence of ultrasonic waves of the other.

The above-mentioned objects are achieved by the following ultrasonic diagnosis apparatus. More specifically, there is provided an ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by the transmission/reception unit to obtain an ultrasonic image having a predetermined dynamic range;

a conversion unit for converting the ultrasonic image having the predetermined dynamic range obtained by the signal processing unit into an ultrasonic image having a dynamic range different from the predetermined dynamic range; and a display unit for displaying the ultrasonic image obtained by the conversion unit.

Also, the above-mentioned objects are achieved by the following ultrasonic diagnosis apparatus. More specifically, there is provided an ultrasonic diagnosis apparatus comprising:

a plurality of ultrasonic probes used for performing transmission/reception of ultrasonic waves for different portions of an object to be examined;

a single transmission/reception unit for driving the plurality of ultrasonic probes to perform transmission/reception so as to obtain ultrasonic images in units of frames each constituted by a plurality of scanning lines;

a switch unit for time-divisionally switching combinations of connections between each of the plurality of ultrasonic probes and the transmission/reception unit;

a setting unit for setting a region of interest in the ultrasonic images in units of frames;

a calculation unit for substantially simultaneously calculating a plurality of temporal change curves of image data in the regions of interest, set by the setting unit, of the ultrasonic images in units of frames; and a display unit for simultaneously displaying temporal change curves calculated by the calculation unit.

Furthermore, the above-mentioned objects are achieved by the following ultrasonic diagnosis apparatus. More specifically, there is provided an ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by the transmission/reception unit to obtain an ultrasonic image;

setting means for setting a region of interest in the ultrasonic image obtained by the signal processing unit;

means for substantially simultaneously calculating a plurality of temporal change curves of image data in the region of interest set by the setting means; and a display unit for simultaneously displaying the ultrasonic image obtained by the signal processing unit and the plurality of temporal change curves obtained by the means.

Moreover, the above-mentioned objects are achieved by the following ultrasonic diagnosis apparatus. More specifically, there is provided an ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by the transmission/reception unit to obtain ultrasonic images in units of frames;

a setting unit for setting regions of interest in the ultrasonic images in units of frames obtained by the signal processing unit;

a filtering unit for filtering the regions of interest in units of frames set by the setting means;

a calculation unit for calculating a temporal change curve of image data in the regions of interest on the basis of image data in the regions of interest in units of frames filtered by the filtering unit; and a display unit for displaying the temporal change curve calculated by the calculation unit.

According to the present invention, an ultrasonic image with a desired dynamic range can be acquired. Therefore, even an ultrasonic image acquired from an object to be examined into which a contrast medium is injected can be displayed on the display unit without being saturated. Therefore, the contrast medium component of a reception signal can be prevented from being saturated beyond the upper limit of the dynamic range.

According to the present invention, since the plurality of ultrasonic probes are time-divisionally driven by the single transmission/reception unit to perform transmission/reception, each ultrasonic probe can be prevented from being influenced by ultrasonic waves generated from other ultrasonic probes, and temporal change curves of a plurality of regions of interest can be simultaneously displayed under the same transmission/reception conditions. Therefore, various kinds of information such as a change, over time, in flow-in/out amount of a contrast medium in/from a region of interest can be displayed in real time.

Furthermore, according to the present invention, a plurality of temporal change curves of a plurality of regions of interest in a single ultrasonic image can be simultaneously acquired and displayed. Therefore, images of two separate portions can be acquired in real time while supplying generation of beat noise components in each image due to the influence of ultrasonic waves of the other.

Moreover, a temporal change curve of image data in a region of interest can be displayed on the basis of image data of the region of interest, which data are filtered between frames.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7 is a block diagram showing the arrangement of a contrast medium signal detector shown in FIG. 3;

FIGS. 9A and 9B are views showing frames before and after an ROI marker is added to an image;

FIG. 10 is a view for explaining average value calculation processing by an average value calculator shown in FIG. 7;

FIG. 15 is a block diagram showing the arrangement of a modification of the third embodiment;

FIG. 19 is a block diagram showing the arrangement of the fourth embodiment;

FIG. 21 is a block diagram showing the arrangement according to the fifth embodiment of the present invention;

FIG. 22 is a block diagram showing another arrangement of the fifth embodiment;

DETAILED DESCRIPTION OF THE PREFERRED EMBODIMENTS

The preferred embodiments of an ultrasonic diagnosis apparatus according to the present invention will be described hereinafter with reference to the accompanying drawings.

Figure 1:
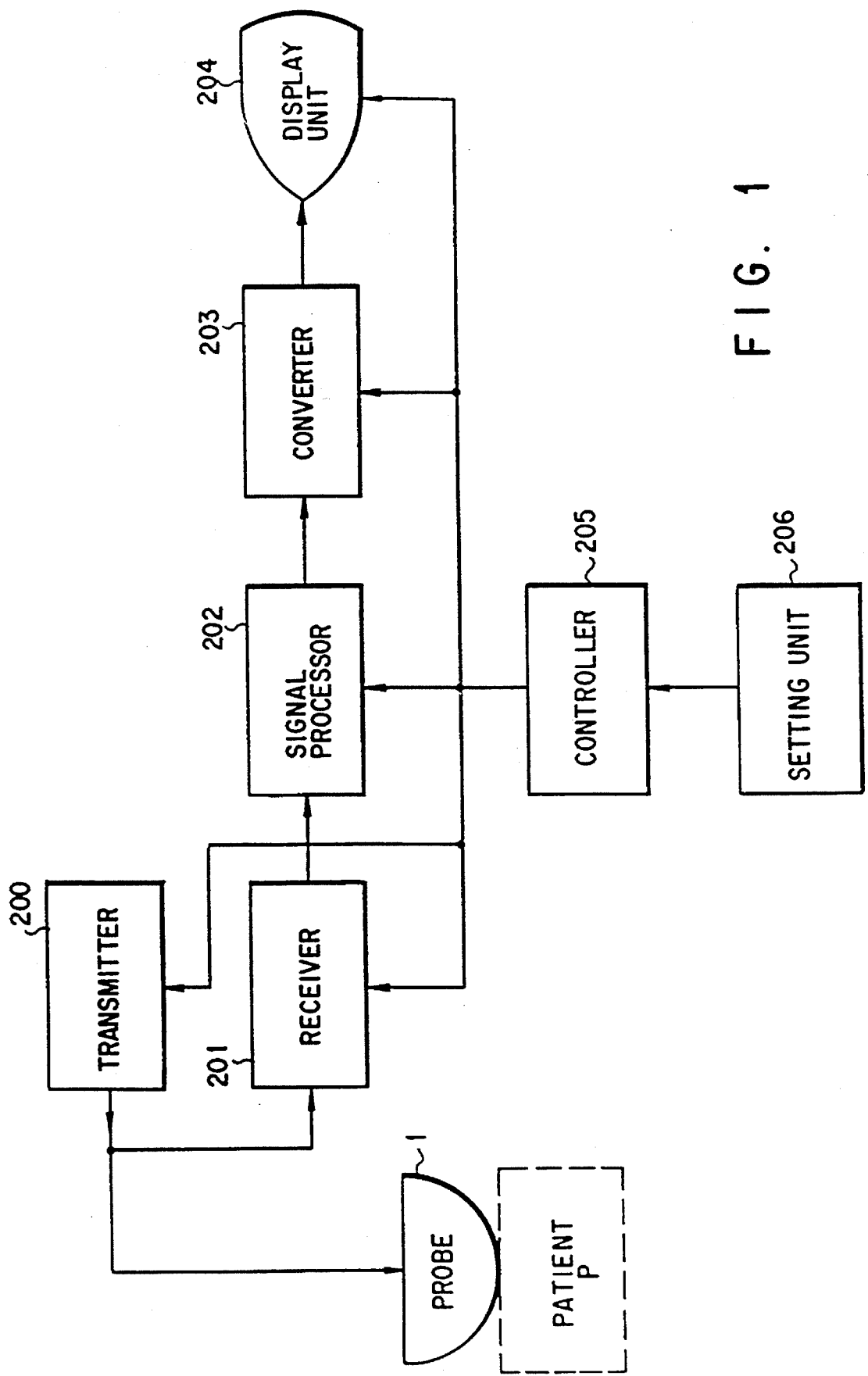
FIG. 1 is a block diagram showing the arrangement of an ultrasonic diagnosis apparatus according to the first embodiment of the present invention.

FIG. 1 is a block diagram showing an ultrasonic diagnosis apparatus according to the first embodiment of the present invention. As shown in FIG. 1, an ultrasonic probe 1 which is brought into contact with an object P to be examined (to be referred to as a patient P hereinafter) is driven by a transmitter 200 and a receiver 201 to perform transmission/reception. An ultrasonic reception signal is obtained from the receiver 201. The ultrasonic reception signal is supplied to a signal processor 202, and the processor 202 can acquire an ultrasonic image such as a B-mode image, a Doppler image, a CFM (color flow mapping) image, or the like. A converter 203 converts the dynamic range of the ultrasonic image output from the signal processor 202. A display unit 204 displays the ultrasonic image having the converted dynamic range. A controller 205 controls the transmitter 200, the receiver 201, the signal processor 202, the converter 203, and the display unit 204.

A setting unit 206 sets diagnosis conditions such as an ultrasonic condition. In addition, the setting unit 206 supplies a command to the controller 205 to change the conversion characteristics of the converter 203 in correspondence with an ultrasonic image in a contrast medium mode acquired from a patient into which a contrast medium is injected, and an ultrasonic image in a normal mode acquired from a patient into which no contrast medium is injected. The converter 203 properly selectively uses the normal mode and the contrast medium mode using two log compressors having different dynamic ranges. In the normal mode, the converter 203 can acquire an ultrasonic image having a high contrast, and in the contrast medium mode, the converter 203 can log-compress an ultrasonic image without saturating a contrast medium signal.

Figure 2:
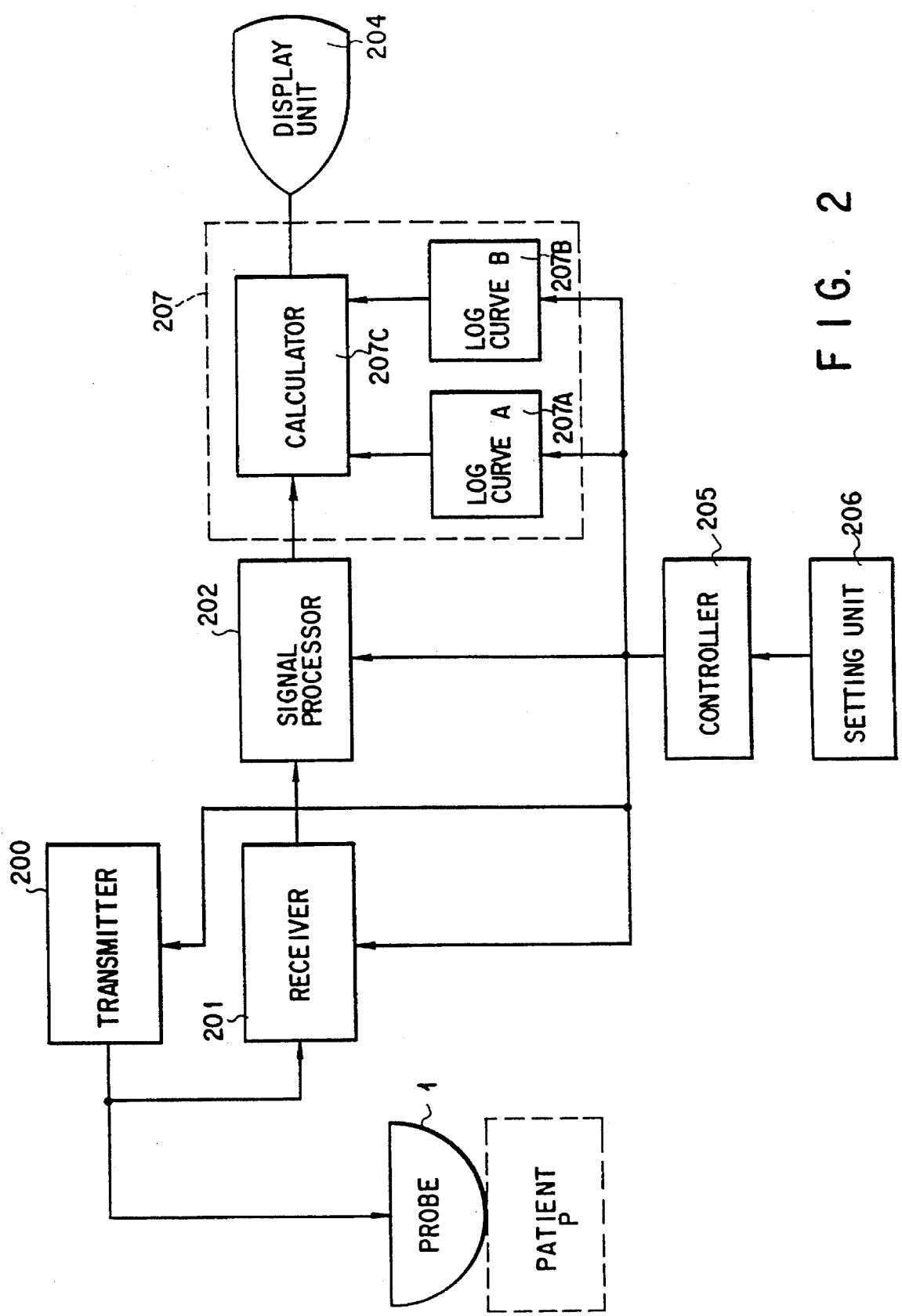
FIG. 2 is a block diagram showing the arrangement of an ultrasonic diagnosis apparatus according to the second embodiment of the present invention.

FIG. 2 is a block diagram showing an ultrasonic diagnosis apparatus according to the second embodiment of the present invention. As shown in FIG. 2, the ultrasonic diagnosis apparatus of the second embodiment comprises a converter 207 different from that in the ultrasonic diagnosis apparatus of the first embodiment. The converter 207 comprises a memory 207A for storing one log-compression curve data, a memory 207B for storing the other log-compression curve data, and a calculator 207C. For example, one log-compression curve data represents log-compression characteristics to be used in the normal mode, and the other log-compression curve data represents log-compression characteristics to be used in the contrast medium mode. The converter 207 converts an input value into a predetermined output value on the basis of the log-compression curve data. Therefore, the converter 207 log-compresses an input value, and outputs the log-compressed value. The converter 207 can also acquire an ultrasonic image having a high contrast in the normal mode and can log-compress an ultrasonic image without saturating a contrast medium signal in the contrast medium mode by selectively using the normal and contrast medium modes.

Figure 3:
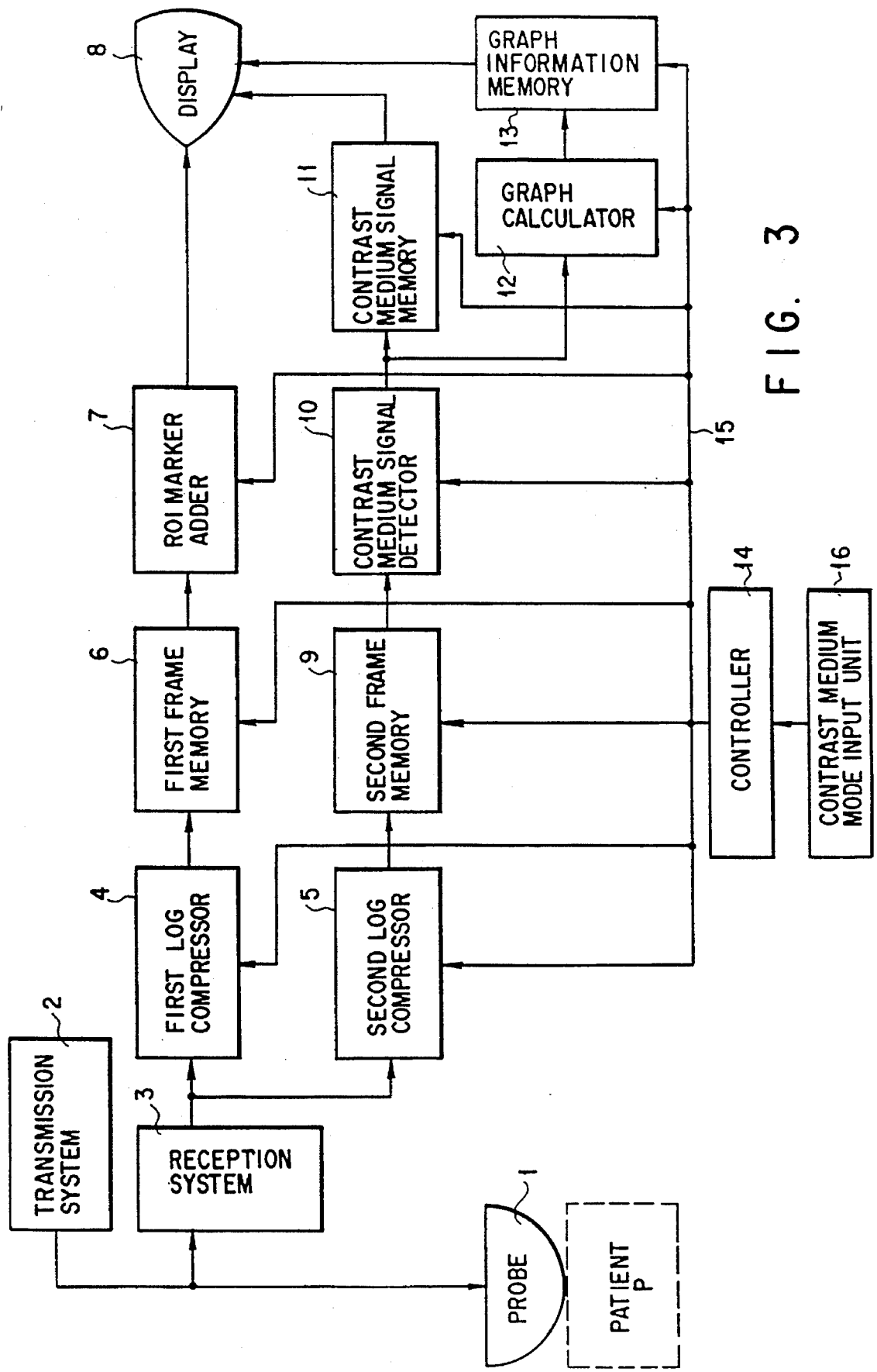
FIG. 3 is a block diagram showing the arrangement of an ultrasonic diagnosis apparatus according to the third embodiment of the present invention.

FIG. 3 is a block diagram showing an ultrasonic diagnosis apparatus according to the third embodiment of the present invention. A sector type electron scanning probe 1 comprises a plurality of linearly arranged vibrators. Note that the probe 1 is not limited to the sector type electron scanning probe, but may be a linear type probe or a mechanical scanning probe. The probe 1 is connected to a transmission system 2. The transmission system 2 supplies driving pulses to the vibrators of the probe 1. The transmission system 2 varies the output timings of the driving pulses among the vibrators, thereby causing the probe to transmit ultrasonic beams in arbitrary directions.

waves reflected by a patient P are received by the same vibrators as the vibrators which transmitted the ultrasonic waves, and reception signals are supplied to a reception system 3. The reception system 3 gives a delay time opposite to that upon transmission to the reception signals and adds the reception signals. The outputs of the reception system 3 are connected to two log compressors 4 and 5. The first log compressor 4 is enabled in the normal mode, and the second log compressor 5 is enabled in the contrast medium mode. The log compressors 4 and 5 log-compress the outputs from the reception system 3 in accordance with equation (1) below, and output the compressed results as luminance information:

$$\theta = A \cdot \log DR \cdot I \tag{1}$$

where $\theta$ is the output from the log compressor, $I$ is the input to the log compressor, $A$ is a predetermined coefficient, and DR is a parameter for determining the compression ratio.

Figure 5:
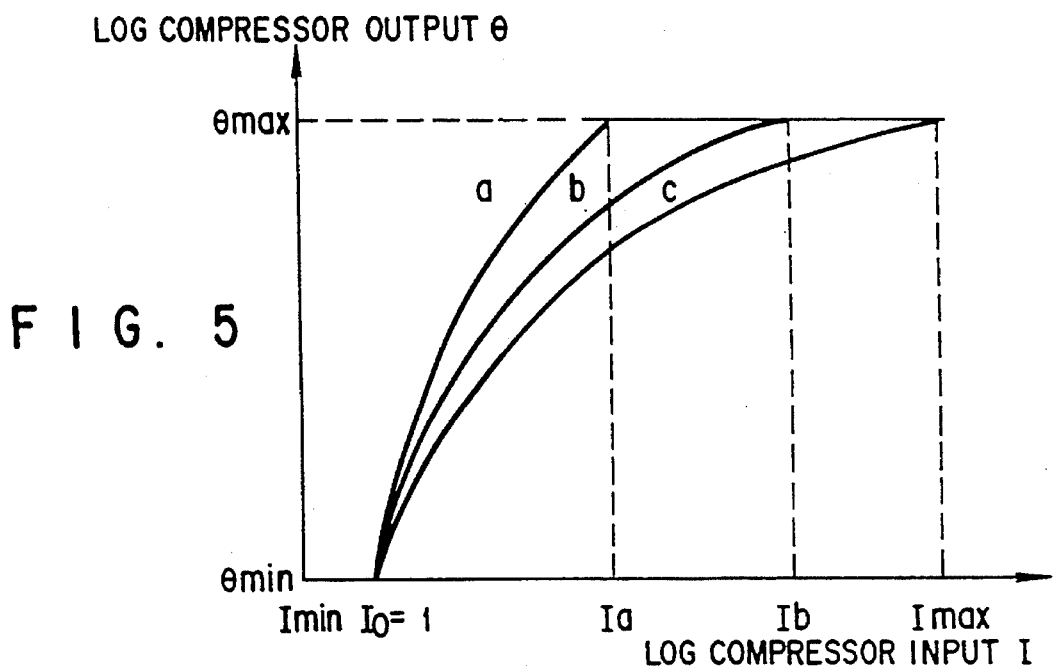
FIG. 5 is a graph showing the dynamic range of a log compressor shown in FIG. 3.

The first and second log compressors 4 and 5 have different parameters DR. The first log compressor 4 uses a parameter DR1 or DR2 (DR1<DR2). The second log compressor 5 uses a parameter DR3 larger than the parameter DR2. Each of the log compressors 4 and 5 has a fixed input range from $I_{min}$ to $I_{max}$, and a fixed output range from $\theta_{min}$ to $\theta_{max}$. Therefore, when the log compression result is smaller or larger than the lower or upper limit of the output range from $\theta_{min}$ to $\theta_{max}$, the output is normalized to $I_{min}$ or $I_{max}$. FIG. 5 shows log curves a, b, and c corresponding to the parameters DR1, DR2, and DR3, and their dynamic ranges. The dynamic range for the parameter DR1 ranges from $I_0$ to $I_a$, the dynamic range for the parameter DR2 ranges from $I_0$ to $I_b$, and the dynamic range for the parameter DR3 ranges from $I_0$ to $I_{max}$.

Therefore, the dynamic range of the second log compressor 5 is wider than that of the first log compressor 4, and the second log compressor 5 can log-compress a contrast medium signal without being saturated.

The output from the first log compressor 4 is supplied to a first frame memory 6, and is developed on a two-dimensional matrix. Then, the developed data is linearly output from the first frame memory 6 in a predetermined order. The output from the first frame memory 6 is supplied to a display 8 via an ROI marker adder 7.

The output from the second log compressor 5 is supplied to a second frame memory 9, and is developed on a two-dimensional matrix. Then, the developed data is linearly output from the second frame memory 9 in a predetermined order. The output from the second frame memory 9 is supplied to a contrast medium signal detector 10. The contrast medium signal detector 10 extracts a contrast medium component (to be referred to as a "contrast medium signal" hereinafter) from the output from the second frame memory 9. The contrast medium signal is supplied to the display 8 via a contrast medium signal memory 11.

This contrast medium signal is also supplied to a graph calculator 12. The graph calculator 12 creates graph information of a curve representing a change, over time, in flow-in/out amount of a contrast medium to/from a region of interest (ROI) (to be referred to as a "time-density curve" hereinafter) using the contrast medium signal, and measures various kinds of time information such as a flow-in time, flow-out time, and the like. The output from the graph calculator 12 is supplied to the display 8 via a two-dimensional graph information memory 13.

A controller 14 supplies control signals and required information to the log compressors 4 and 5, the frame memories 6 and 9, the ROI marker adder 7, the contrast medium signal detector 10, the contrast medium signal memory 11, the graph calculator 12, and the graph information memory 13 via a bus line 15 to operate them in association with each other and to cause them to execute corresponding processing.

Figure 4:
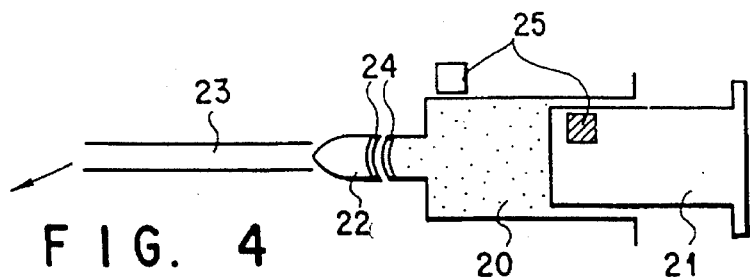
FIG. 4 is a sectional view showing an example of a contrast medium mode input unit shown in FIG. 3.

A contrast medium mode input unit 16 is a device used for inputting an instruction for switching between the normal mode and the contrast medium mode. The switching operation between the normal mode and the contrast medium mode may be performed depending on a key operation on a keyboard or on the output from a switch for detecting if a contrast medium injection device is started. The contrast medium injection device is mainly constituted by a syringe which comprises a cylindrical portion 20 having a projecting port at one end and an insertion port at the other end, and an insertion portion 21 to be inserted in the cylindrical portion 20, as shown in FIG. 4. When a contrast medium is to be injected using the contrast medium injection device, the insertion portion 21 is inserted deep in the cylindrical portion 20, or a tube 23 is connected to the projecting port via a joint 22. Therefore, when an electrode switch 24 for detecting if the tube 23 is connected to the projecting port is arranged on the joint 22 or an electromagnetic switch 25 is arranged on the syringe, it can be detected if the contrast medium injection device is started. The electrode switch 24 outputs an ON signal when the tube 23 is connected to the projecting port. The electromagnetic switch 25 comprises a magnet arranged near the distal end of the insertion portion 21, and a coil arranged in the cylindrical portion 20 at a position where the coil faces the magnet when the insertion portion 21 is inserted deep in the cylindrical portion 20. Thus, the electromagnetic switch 25 generates an induction current generated in the coil when the insertion portion 21 is inserted deep in the cylindrical portion 20, and detects that the contrast medium injection device is started. The switch 25 then outputs an ON signal. Upon reception of the ON signal, the controller 14 switches the operation mode from the normal mode to the contrast medium mode.

Figure 6:
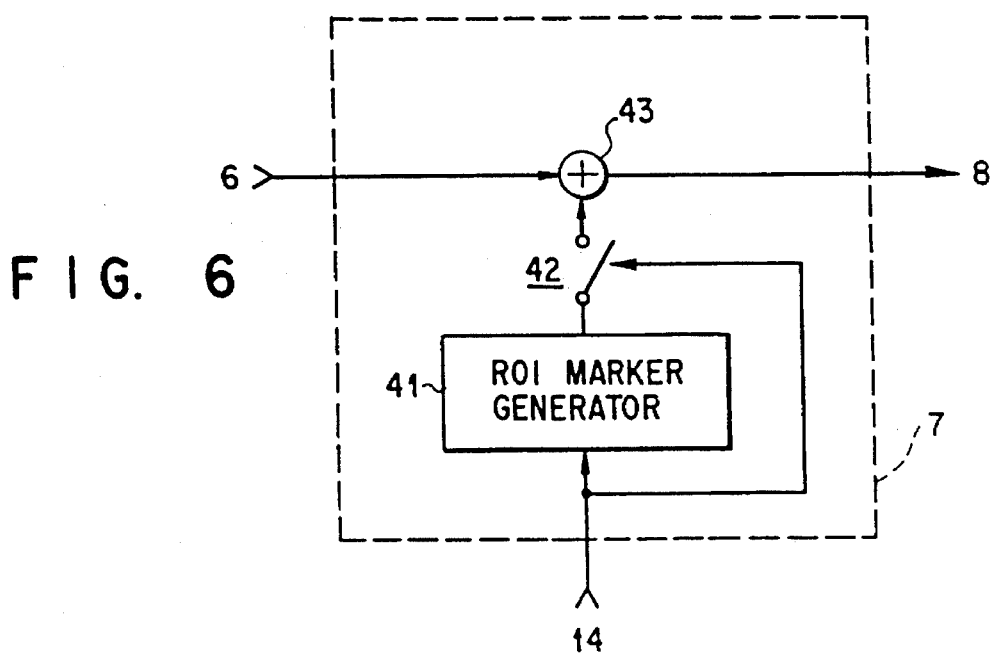
FIG. 6 is a block diagram showing the arrangement of an ROI marker adder shown in FIG. 3.

FIG. 6 is a block diagram showing the arrangement of the ROI marker adder 7. An ROI marker generator 41 receives marker information from the controller 14. The marker information is input when an operator operates an input device such as a mouse (not shown) connected to the controller 14. The ROI marker generator 41 outputs, e.g., rectangular marker data representing a region of interest on the basis of the marker information. The marker data is supplied to an adder 43 via a switch 42, and is synthesized with an image from the first memory 6. The switch 42 is opened/closed in correspondence with a control signal from the controller 14, and connects the ROI marker generator 41 to the adder 43 when marker data based on the marker information is output from the ROI marker generator 41. The output from the adder 43 is supplied to the display 8.

FIG. 7 is a block diagram showing the arrangement of the contrast medium signal detector 10. An image (to be referred to as an "ROI image" hereinafter) in a region of interest (ROI) is output from the second frame memory 9. The ROI image is supplied to a subtracter 57 directly and via an average value calculator 51 and an ROI frame average value memory 56. The subtraction result of the subtracter 57 is supplied to an accumulation adder 60 and a frame difference value memory 63 as a frame difference value, i.e., a contrast medium signal. The outputs from the accumulation adder 60 and the frame difference value memory 63 are selectively supplied to the contrast medium signal memory 11 and the graph calculator 12 via a switch 64. The average value calculator 51 is a means for calculating an average value of pixels in the region of interest (ROI) of a predetermined number of frames, and comprises an adder 52, an ROI frame memory 53, a switch 54, and a divider 55. The adder 52 adds an ROI image input from the second frame memory 9 and a sum image input from the ROI frame memory 53 via the switch 54 in units of pixels, and supplies the sum image to the ROI frame memory 53. The switch 54 connects the ROI frame memory 53 to the adder 52 until addition of ROI images corresponding to the predetermined number of frames is completed, thereby adding the ROI images corresponding to the predetermined number of frames. The sum image is divided with the number of added frames by the divider 55, i.e., is subjected to average processing. Note that the average processing is performed to eliminate a temporal variation in contrast medium signal and to remove spike noise components. The average image is supplied to the subtracter 57 via the ROI frame average value memory 56 and its polarity is inverted by a −1 multiplier 58 of the subtracter 57. Thereafter, the polarity-inverted image is added to the ROI image from the second frame memory 9 by an adder 59 in units of pixels. With this processing, a contrast medium signal included in the ROI image is detected in units of pixels, thus generating a contrast medium image. The contrast medium image is supplied to the accumulation adder 60 and the frame difference value memory 63. The accumulation adder 60 comprises a frame difference value memory 63 which is feed-back connected to an adder 61, and accumulates the contrast medium image in units of pixels. The outputs from the accumulation adder 60 and the frame difference value memory 63 are selectively read out upon switching of the switch 64, and the selected output is supplied to the contrast medium signal memory 11 and the graph calculator 12. The switching operation of the switch 64 is performed in accordance with a display switching instruction input by an observer via an input device (not shown). The output from the contrast medium signal memory 11 is supplied to the display 8.

Figure 8:
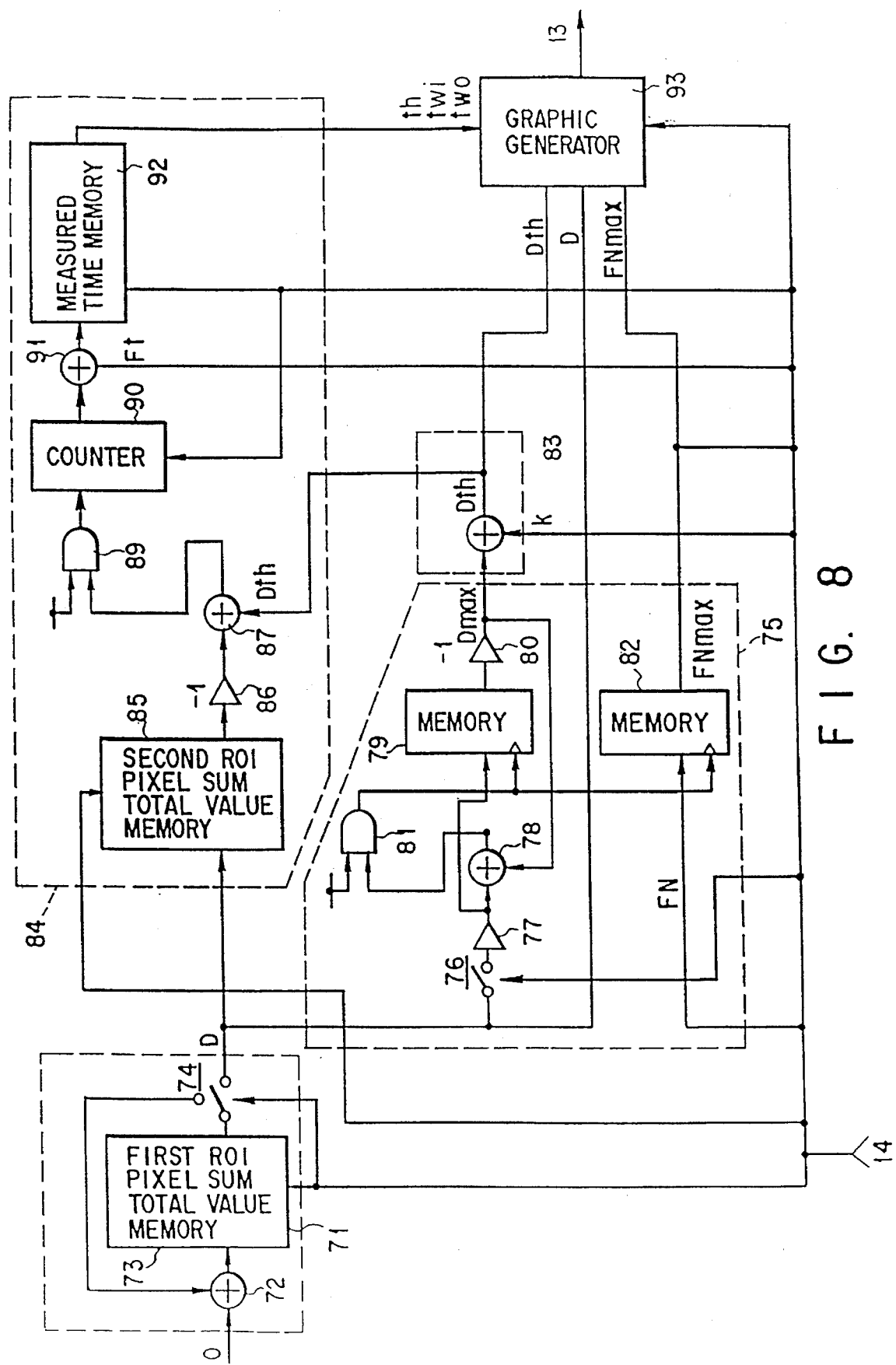
FIG. 8 is a block diagram showing the arrangement of a graph calculator shown in FIG. 3.

FIG. 8 is a block diagram showing the arrangement of the graph calculator 12. The output from the contrast medium signal detector 10 is supplied to a sum total value calculator 71. The sum total value calculator 71 is constituted by feed-back connecting, via a switch 74, a first ROI pixel sum total value memory 73 to an adder 72 connected to the output of the contrast medium signal detector 10. The calculator 71 adds contrast medium signals of all pixels in the ROI to obtain a sum total value D.

A max hold unit 75 detects a maximum value $D_{max}$ of a plurality of sum total values D sequentially output from the sum total value calculator 71, and its frame number $FN_{max}$, and temporarily stores them. The latest sum total value D from the sum total value calculator 71 is inverted via a switch 76 and a −1 multiplier 77, and the inverted value is supplied to an adder 78 and a memory 79. The adder 78 adds the latest sum total value D to the previous sum total value D which is supplied from the memory 79 and is inverted again via a −1 multiplier 80. An AND gate 81 logically discriminates the polarity of the output from the adder 78, i.e., which of the latest sum total value D and the previous sum total value D is larger, and outputs the discrimination result to the memory 79 as update control information of the memory 79. When the discrimination result indicates that the latest sum total value D is larger than the previous sum total value D, the memory 79 stores the latest sum total value D in place of the previous sum total value D. Therefore, the memory 79 always stores the maximum value $D_{max}$ of a plurality of sum total values D supplied so far. The discrimination result of the AND gate 81 is also supplied to the other memory 82, and a frame number FN to be stored in the memory 82 is updated in correspondence with the discrimination result. With this processing, the memory 82 stores the frame number $FN_{max}$ corresponding to the maximum value $D_{max}$ stored in the memory 79. Note that the memory 82 receives the frame number FN corresponding to the latest sum total value D from the controller 14.

The maximum value $D_{max}$ is supplied to a multiplier 83 of a threshold value generator 83. The multiplier 83 multiplies the maximum value $D_{max}$ with a threshold value coefficient K (normally, ½) supplied from the controller 14, and outputs a threshold value $D_{th}$. The threshold value $D_{th}$ is supplied to a time measurement unit 84.

The time measurement unit 84 comprises a second ROI pixel sum total value memory 85 for storing a plurality of continuous sum total values D output from the sum total value calculator 71. The second ROI pixel sum total value memory 85 sequentially outputs the sum total values in the input order. The output from the second ROI pixel sum total value memory 85 is inverted via a −1 multiplier 86, and the inverted value is supplied to an adder 87. The adder 87 adds the inverted value to the threshold value $D_{th}$. The sum is supplied to an AND gate 89, and its polarity is logically discriminated. As a result of discrimination, if the sum total value D is larger than the threshold value $D_{th}$, the value of a counter 90 is incremented by 1. The counter 90 executes independent count operations before and after the frame number $FN_{max}$ under the control of the controller 14. With these operations, the counter 90 counts the number of frames having sum total values D equal to or larger than the threshold value $D_{th}$ before the frame of the maximum value $D_{max}$, and the number of frames having sum total values D equal to or larger than the threshold value $D_{th}$ after the frame of the maximum value $D_{max}$. These numbers of frames are independently multiplied by a multiplier 91 with a frame period time $F_t$ upon transmission/reception of ultrasonic waves, which time is supplied from the controller 14, so as to be converted into real times. The real time based on the former number of frames will be referred to as a flow-in time $t_{wi}$ representing a time required until the contrast medium flows into the ROI hereinafter, the real time based on the latter number of frames will be referred to as a flow-out time $t_{wo}$ representing a time required until the contrast medium flows out from the ROI hereinafter, and the total time of these flow-in and flow-out times $t_{wi}$ and two will be referred to as a half-width time $t_h$ hereinafter. The flow-in time $t_{wi}$, the flow-out time $t_{wo}$, and the half-width time $t_h$ are output to a graphic generator 93 via a measured time memory 92.

The graphic generator 93 sequentially receives the sum total values D from the sum total value calculator 71, and gradually completes a time-density curve by plotting points along the time base in correspondence with the sum total values D. The time-density curve is output to the display 8 every time a point is plotted, even if it is not completed yet. Therefore, on the display 8, the time-density curve gradually grows until it is completed.

The operation of this embodiment will be explained below.

The normal mode is started first. In the normal mode, the first log compressor 4 is enabled. A section of the patient P is repetitively scanned by ultrasonic beams from the probe 1 in accordance with a driving signal from the transmission system 2. Waves reflected by the patient P are received by the probe 1, and reception signals are sequentially output to the first log compressor 4 via the reception system 3. The first log compressor 4 log-compresses the reception signals using the parameter DR1 or DR2, as described above, and supplies the compression results to the first frame memory 6. Therefore, the reception signals of a living body tissue are optimally log-compressed with respect to the output range, and an image with a high contrast can be acquired. In the normal mode, the switch 42 of the ROI marker adder 7 is set in the OFF state. Therefore, the image in the first frame memory 6 is displayed on the display 8, as shown in FIG. 9A.

An operator switches the operation mode from the normal mode to the contrast medium mode at an arbitrary timing. This switching operation is performed depending on the key operation on the keyboard of the contrast medium mode input unit 16 or the output from the switch for detecting if the contrast medium injection device is started, as described above. Even after the operation mode is switched from the normal mode to the contrast medium mode, ultrasonic scanning still continues. Before or after the contrast medium mode is set, the switch 42 of the ROI marker adder 7 is set in the ON state, and an ROI (broken line) is displayed while being superposed on the image, as shown in FIG. 9B. The ROI is set at an arbitrary position by the operator. In the contrast medium mode, the second log compressor 5 operates in place of the first log compressor 4. As described above, the second log compressor 5 log-compresses reception signals using the parameter DR3 larger than the parameter DR1 or DR2 of the first log compressor 4. Therefore, the dynamic range of the second log compressor 5 is wider than that of the first log compressor 4, and with this dynamic range, a contrast medium signal having a higher signal level than that from a living body tissue can be log-compressed without being saturated.

Figure 11A:
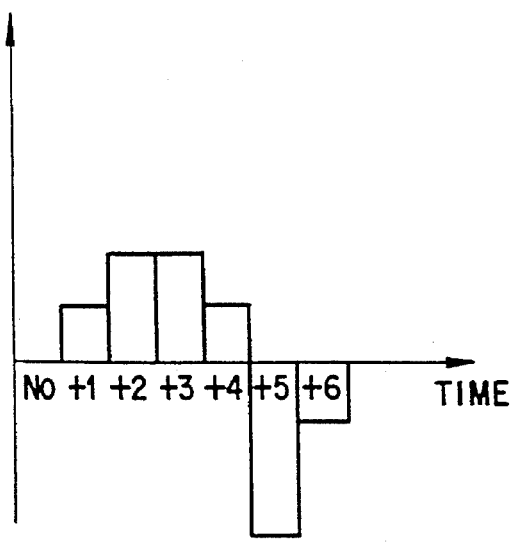
FIGS. 11A and 11B are graphs showing two different signals, i.e., change amounts between frames of a contrast medium signal output from the contrast medium signal detector shown in FIG. 3, and accumulated values of the change amounts.
Figure 11B:
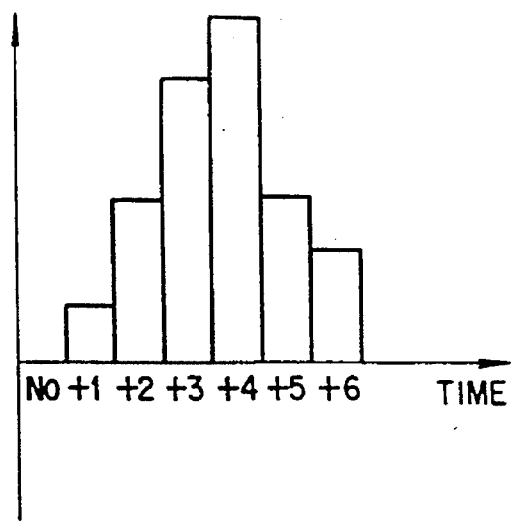
Figure 12A:
FIGS. 12A to 12D are views showing changes in display screen until the beginning of time measurement.
Figure 12B:
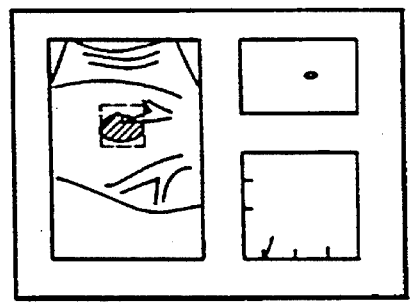
Figure 12C:
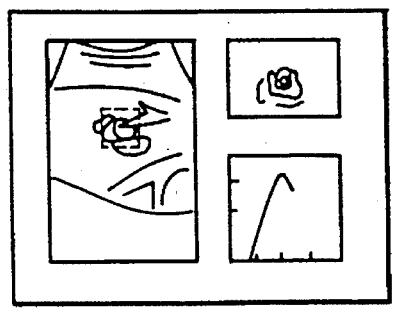
Figure 12D:
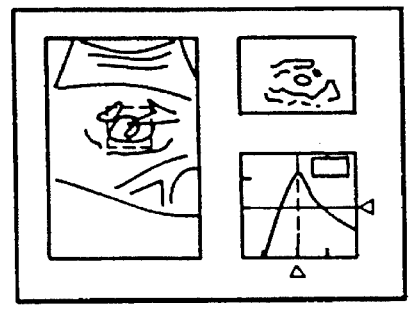

The output from the second log compressor 5 is supplied to the second frame memory 9. An image in the ROI is selectively read out from the second frame memory 9 and is supplied to the contrast medium signal detector 10. The ROI image is supplied to the subtracter 57 and the average value calculator 51 in the contrast medium signal detector 10. The switch 54 of the average value calculator 51 is connected to the adder 52 side until ROI images corresponding to a predetermined number of frames are input. Therefore, in the ROI frame memory, ROI images corresponding to a predetermined number of frames including an ROI image of the latest frame are added in units of pixels. FIG. 10 shows the outline of this addition processing. Upon completion of this addition, the switch 54 is connected to the divider 55 side, and the sum is supplied to the divider 55. The divider 55 divides the sum image with the number of added frames, i.e., executes average processing, thereby eliminating a temporal change in contrast medium signal, and removing spike noise components. The divider 55 then supplies the average image to the subtracter 57 via the ROI frame average value memory 56. The subtracter 57 subtracts the average image from the ROI image of the latest frame. Pixels of the ROI image before subtraction include both living body tissue components and contrast medium components. Since the living body tissue components do not change over time, the living body tissue components and the contrast medium components up to the previous frame are removed by subtracting the average image from the ROI image of the latest frame. Thus, the change amounts of contrast medium components from the previous frame are detected in units of pixels, and a contrast medium image is generated. Paying attention to a certain pixel in the contrast medium image, its value changes over time, as shown in FIG. 11A. The contrast medium image is supplied to and stored in the frame difference value memory 63. The contrast medium image is also supplied to the accumulation adder 60 to accumulate sequentially supplied contrast medium images in units of pixels. Paying attention to a certain pixel in the accumulated image, its value changes over time, as shown in FIG. 11B. More specifically, the accumulation result corresponds to the total amount of the contrast medium currently present in the ROI. The frame difference value memory 63 and the accumulation adder 60 are selectively connected to the contrast medium signal memory 11 and the graph calculator 12 via the switch 64. The switching operation of the switch 64 is performed in accordance with an instruction from an operator. Normally, the switch 64 is connected to the accumulation adder 60. Every time a contrast medium image is input, the accumulation adder 60 outputs an accumulated image in turn, and the accumulated image is displayed on the display 8 while being switched via the contrast medium signal memory 11. FIGS. 12A to 12D show display screens along with the elapse of time. An image is displayed on the left window in each display screen, an accumulated image is displayed on the upper right window in each display screen, and a time-density curve is displayed on the lower right window in each display screen. Since the accumulated images are output in turn every time the contrast medium image is input, the flow-in state of the contrast medium is displayed in real time, as shown in FIGS. 12A to 12D.

The accumulated images are sequentially supplied to the graph calculator 12, and the sum total value calculator 71 calculates the sum total value D of all the pixels of each accumulated image. The sum total values D of frames are sequentially supplied to the max hold unit 75, the time measurement unit 84, and the graphic generator 93. At this time, the switch 76 in the max hold unit 75 is set in the ON state, and the sum total value D in the memory 79 is sequentially updated with a value larger than the sum total value D up to the previous frame. As a result, the memory 79 always stores the maximum value $D_{max}$ of the sum total values D up to the latest frame, and the memory 82 stores the frame number $FN_{max}$ of the maximum value $D_{max}$. The second ROI pixel sum total value memory 85 of the time measurement unit 84 stores all the sum total values D up to the latest frame. The graphic generator 93 gradually creates a time-density curve on the basis of the sequentially supplied total sum values D. The time-density curve under creation is supplied to the display 8 via the graph information memory 13 at respective timings, and the time-density curve is displayed together with the accumulated image while gradually growing in real time in correspondence with the flow-in state of the contrast medium, as shown in FIGS. 12A to 12D.

Figure 13A:
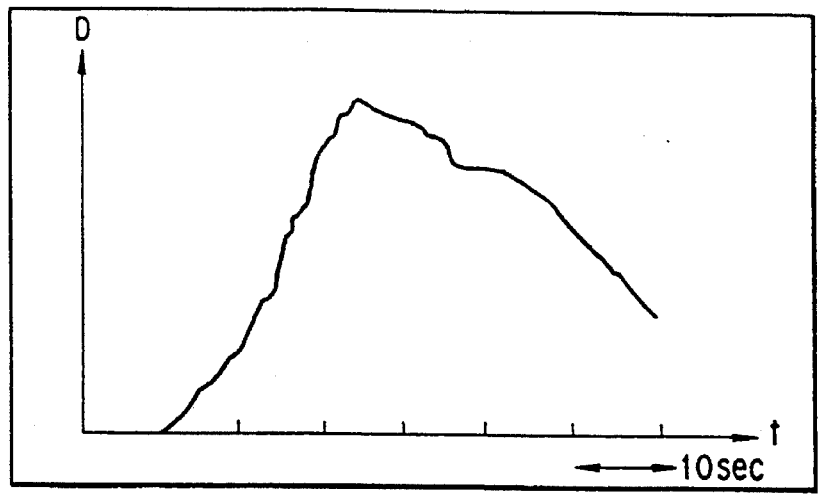
FIGS. 13A and 13B are views showing the display positions for a completed time-density curve and a measurement time.

When the time-density curve has reached a state shown in FIG. 13, and the operator determines from this state that the contrast medium sufficiently has flowed out from the ROI, he or she depresses, e.g., a freeze button of an input device (not shown), thus starting measurement of various times. At this time, the switch 76 in the max hold unit 75 is set in the OFF state, and the maximum hold unit 75 no longer receives the sum total value D of the new frame. Therefore, the memory 79 stores the maximum value $D_{max}$ of the sum total values D of all the frames before the time measurement is started, and the memory 82 stores the frame number $FN_{max}$ of the maximum value $D_{max}$.

The maximum value $D_{max}$ is multiplied with the coefficient K (½) from the controller 14 by the threshold value generator 83, thereby generating the threshold value $D_{th}$.

The threshold value $D_{th}$ is supplied to the adder 87 of the time measurement unit 84. All the sum total values D up to the latest frame, which values are stored in the second ROI pixel sum total value memory 85 of the time measurement unit 84, are supplied from previous ones to the adder 87 via the −1 multiplier 86, and are added to the threshold value $D_{th}$. The polarity of each sum is discriminated by the AND gate 89. If the polarity of the sum is negative, i.e., if a given sum total value D is smaller than the threshold value $D_{th}$, the count value of the counter 90 is counted up. Note that the counter 90 receives the frame number $FN_{max}$ stored in the memory 82 from the controller 14, and executes independent count operations before and after the frame number $FN_{max}$. As a result, the number of frames (to be referred to as the "number of flow-in frames" hereinafter) having sum total values D equal to or larger than the threshold value $D_{th}$ before the frame of the maximum value $D_{max}$, and the number of frames (to be referred to as the "number of flow-out frames" hereinafter) having sum total values D equal to or larger than the threshold value $D_{th}$ after the frame of the maximum value $D_{max}$ are counted.

Figure 13B:
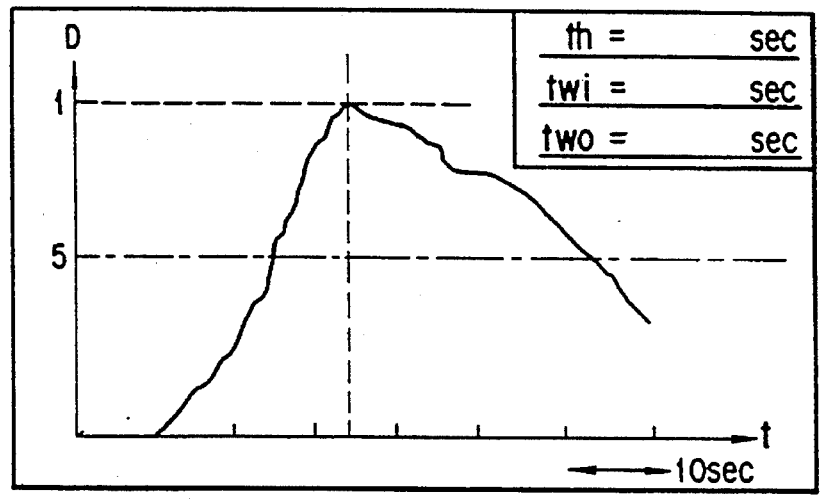
Figure 14:
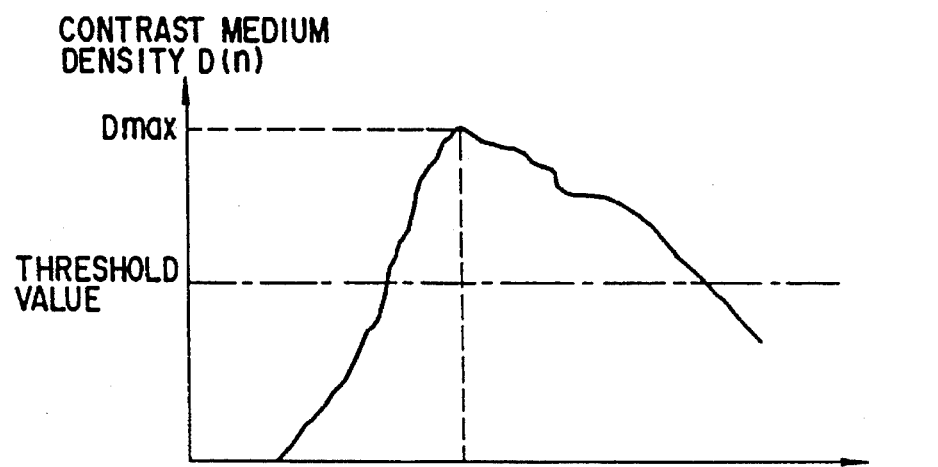
FIG. 14 is a graph showing various times measured by a time measurement unit shown in FIG. 8.

These numbers of frames are independently multiplied with the frame period time $F_t$ upon transmission/reception of ultrasonic waves, which time is supplied from the controller 14, so as to be converted into real times. Therefore, as shown in FIG. 14, the flow-in time $t_{wi}$, the flow-out time $t_{wo}$, and the half-width time $t_h$ as the total time of the flow-in and flow-out times $t_{wi}$ and $t_{wo}$ are measured. The flow-in time $t_{wi}$, the flow-out time $t_{wo}$, and the half-width time $t_h$ are displayed on the display 8 via the measured time memory 92 and the graphic generator 93, as shown in FIG. 13B.

As described above, according to this embodiment, a curve representing a change, over time, in flow-in/out amount of the contrast medium to/from the region of interest (ROI), i.e., the time-density curve can be created in real time, and time information of the flow-in time, the flow-out time, and the half-width time of the contrast medium to/from the region of interest (ROI) can be measured.

In this embodiment, the two log compressors having different dynamic ranges are used, and are properly selectively used in the normal mode and the contrast medium mode. Therefore, an image with a high contrast can be acquired in the normal mode, and a contrast medium signal can be log-compressed without being saturated in the contrast medium mode.

In the above-mentioned embodiment, the two log compressors having different dynamic ranges are used. Alternatively, a single log compressor may be used, and its dynamic range may be switched between the normal mode and the contrast medium mode. As shown in FIG. 15, this arrangement can be realized by arranging a switching signal generator 19 which allows the output from a log compressor 17, which is operable with at least two dynamic ranges, to be selectively supplied to the first and second frame memories 6 and 9 via a switch 18, and performs switching control of the dynamic ranges of the log compressor 17 and the switching operation of the switch 18 between the normal mode and the contrast medium mode under the control of the controller 14.

Figure 16:
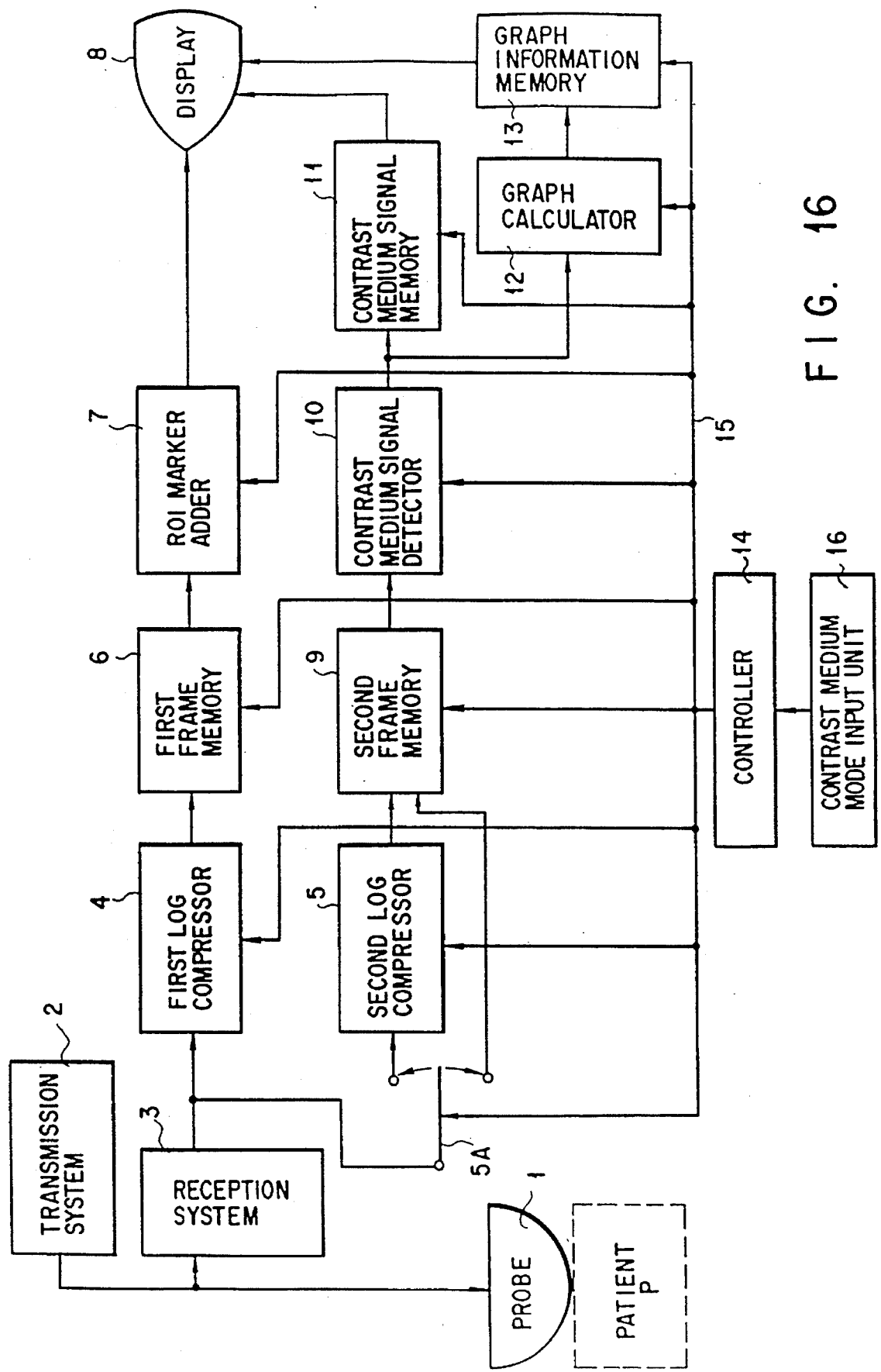
FIG. 16 is a block diagram showing the arrangement of another modification of the third embodiment.

FIG. 16 shows the arrangement of another modification of the third embodiment according to the present invention. In this modification, when the contrast medium mode is set, reception signals are supplied to the second frame memory 9, the contrast medium signal detector 10, the contrast medium signal memory 11, the graph calculator 12, and the graph information memory 13 with or without going through the second log compressor 5 depending on the state of a switch 5A. This arrangement can acquire a curve representing a change, over time, in image data in the ROI in an ultrasonic image whose dynamic range is not adjusted, and a curve representing a change, over time, in image data in the ROI in an ultrasonic image whose dynamic range is adjusted.

Figures 17A, 17B:
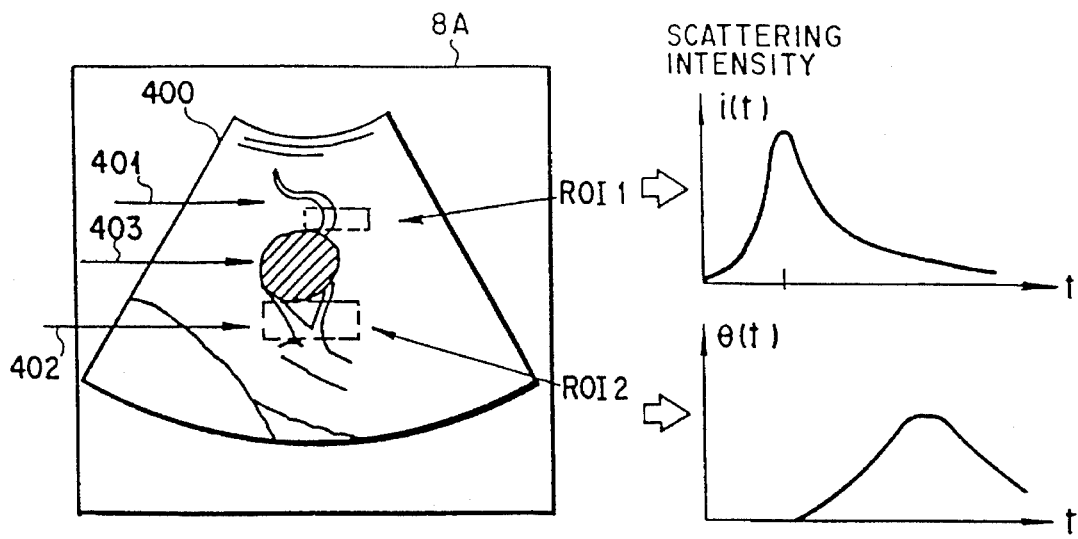
FIG. 17A and 17B are views; and showing the principle according to the fourth embodiment of the present invention.

The fourth embodiment of the present invention will be described below with reference to FIGS. 17 to 20. In the fourth embodiment, a plurality of regions of interest (ROIs) are set in a single ultrasonic image, and time-density curves are created in units of ROIs on the basis of the scattering intensities in the ROIs. Then, for example, the feature amount (clinical data) of an object to be diagnosed, which amount is present between the ROIs, is extracted by calculations, and the clinical data is displayed. In this embodiment, the correlation among time-density curves in units of ROIs must be checked. In addition, a response of an object to be diagnosed, such as a tumor, to blood flow must be quantitized. As shown in FIG. 17, an ultrasonic image 400 is displayed on a screen 8A. The image 400 includes a flow-in path 401 and a flow-out path 402 of a blood vessel, and an object 403 to be diagnosed. A region corresponding to the flow-in path 401 is defined as an ROI1, and a region corresponding to the flow-out path is defined as an ROI2. As shown in the graphs in FIG. 17B, the scattering intensity curves of the ROI1 and ROI2 can be easily obtained by the abovementioned embodiment.

Figure 18A:
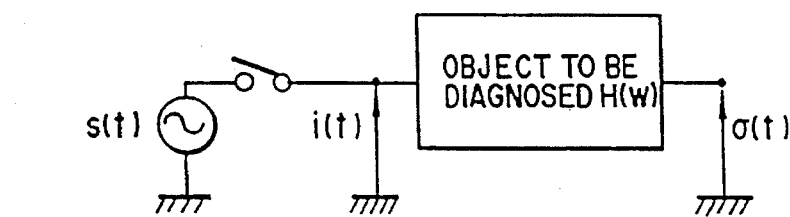
FIG. 18A and 18B are diagrams showing the system model of the fourth embodiment.
Figure 18B:
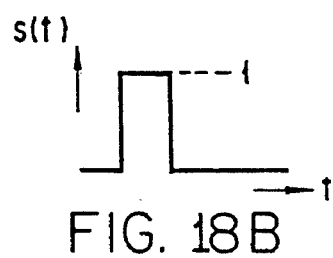

In this case, a system model shown in FIG. 18A and 18B is assumed.

In FIG. 18A, the Fourier transform of a step function s(t) is S(ω), and the inverse Fourier transform of S(ω) is s(t). In FIG. 18B, the Fourier transform of an input function i(t) is I(ω), and the inverse Fourier transform of I(ω) is i(t). The Fourier transform of an output function o(t) is O(ω), and the inverse Fourier transform of O(ω) is o(t). The Fourier transform of a response function h(t) is H(ω), and the inverse Fourier transform of H(ω) is h(t).

H(ω) obtained by Fourier-transforming the response function h(t) to be obtained is given by:

$$H(\omega)=S(\omega)\cdot(O(\omega)/I(\omega))$$

An example of the feature amount includes a time $t_p$ corresponding to a maximum h(t), and a half-width time $t_{1/2}$ of h(t).

FIG. 19 shows the detailed arithmetic blocks of the above-mentioned system model. The system shown in FIG. 19 comprises a Fourier transform unit 301, an S(ω) memory 302, registers 303 to 305 and 307 to 309, an h(t) calculator 306, switches 310 to 312, an adder 313, and a controller 14' which also serves as the above-mentioned controller 14. This system may be realized by either a hardware or software arrangement.

Figure 20:
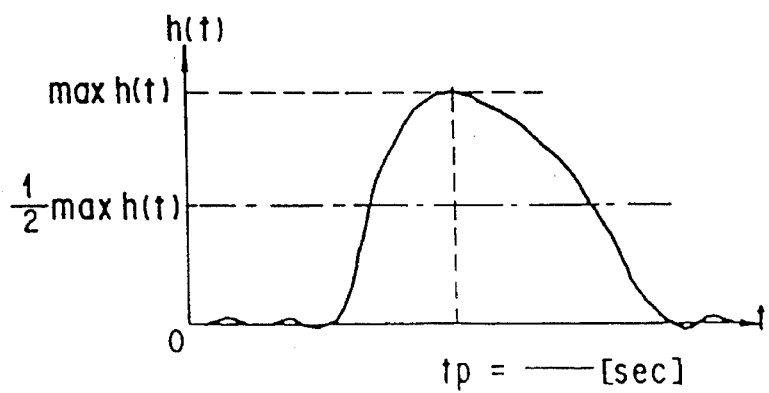
FIG. 20 is a view showing a display example in the fourth embodiment.

With reference to the above equation, the h(t) calculator 306 executes zero divide processing of I(ω), and calculates H(ω), then calculates h(t) by inversely-transforming H(ω).

i(t) and o(t) are input to the Fourier transform unit after the time-density curves are created. FIG. 20 shows a display example of h(t).

The fourth and fifth embodiments will be described below.

In simultaneous observation of two separate portions, e.g., the carotid artery and an internal vein, this embodiment can solve a problem associated with beat noise components generated in each image due to the influence of ultrasonic waves of the other.

The fourth and fifth embodiments may adopt either of the arrangements shown in FIGS. 21 and 22. Either arrangement comprises at least two probes 101 and 102 having the same arrangement. Each of the probes 101 and 102 is constituted by linearly arranging a plurality of vibrators.

In the arrangement of FIG. 21, two systems, i.e., transmission/reception circuits 103 and 104, B-mode processing systems 105 and 106, color flow mapping (CFM) processing systems 107 and 108, and display systems 109 and 110 are arranged in correspondence with the probes 101 and 102, and a monitor 111 is connected to the two display systems 109 and 110. In addition, the arrangement comprises a control circuit 112 for controlling the transmission/reception circuits 103 and 104 to perform transmission/reception driving operations of the probes 101 and 102 simultaneously or time-divisionally in units of frames or rasters (scanning lines) so as not to generate beat noise components in each image due to the influence of ultrasonic waves of the other. Each of the B-mode processing systems 105 and 106 has the same arrangement as that shown in FIG. 3. These systems generate B-mode images, creates time-density curves, and measures various times.

Each of the B-mode processing systems 105 and 106 has the same arrangement as that shown in FIG. 3. More specifically, two log compressors having different dynamic ranges are connected to the outputs of the transmission/reception circuits 103 and 104 to log-compress the outputs from these circuits 103 and 104, and output the compression results as luminance information to the display systems 109 and 110 via an ROI marker adder.

A first frame memory is connected to the output of the first log compressor. The output from the second log compressor is supplied to a contrast medium signal detector for detecting a contrast medium component via a second frame memory. The contrast medium signal is supplied to the display systems 109 and 110 via a two-dimensional contrast medium signal memory. The contrast medium signal is also supplied to a graph calculator. The graph calculator creates a time-density curve using the contrast medium signal, and measures various kinds of time information such as the flow-in time, the flow-out time, and the like of the contrast medium. The output from the graph calculator is supplied to the display systems 109 and 110 via a two-dimensional graph information memory.

Each of the CFM processing systems 107 and 108 comprises a phase detector, an A/D converter, an MTI (Moving-Target-Indicator) filter, an autocorrelator, and a calculator, although not shown. The phase detector performs orthogonal phase detection of a reception signal received from a reception system, and removes high-frequency components using a low-pass filter (not shown) to obtain a Doppler transition signal, i.e., a Doppler detection output for a blood flow image. The Doppler detection output includes an unnecessary reflection signal (clutter components) from a slow-moving object such as a cardiac wall in addition to blood flow information. Thus, the Doppler detection output is converted into a digital signal by the A/D converter, and the digital signal is filtered through the MTI filter.

Note that "MTI" is the technique used in a radar, is an abbreviation of "Moving-Target-Indicator", as described above, and is a method of detecting only a moving target using the Doppler effect. Therefore, the MTI filter detects the motion of the blood flow on the basis of a phase change between identical pixels in response to rate pulses which are repetitively transmitted a predetermined number of times, thereby removing clutter components. The autocorrelator performs frequency analysis of the signals, from which clutter components are removed, in real time in units of points on a two-dimensional matrix. The number of calculations in frequency analysis by the autocorrelator is very smaller than that in the FFT (fast Fourier transform) method, and hence, real-time processing is realized. The calculator receives the output from the autocorrelator, and comprises an average speed calculator, a variance calculator, and a power calculator. In this calculator, the average speed calculator calculates an average Doppler shift frequency fd, the variance calculator calculates a variance $\sigma^2$, and the power calculator calculates a power P.

Figure 23:
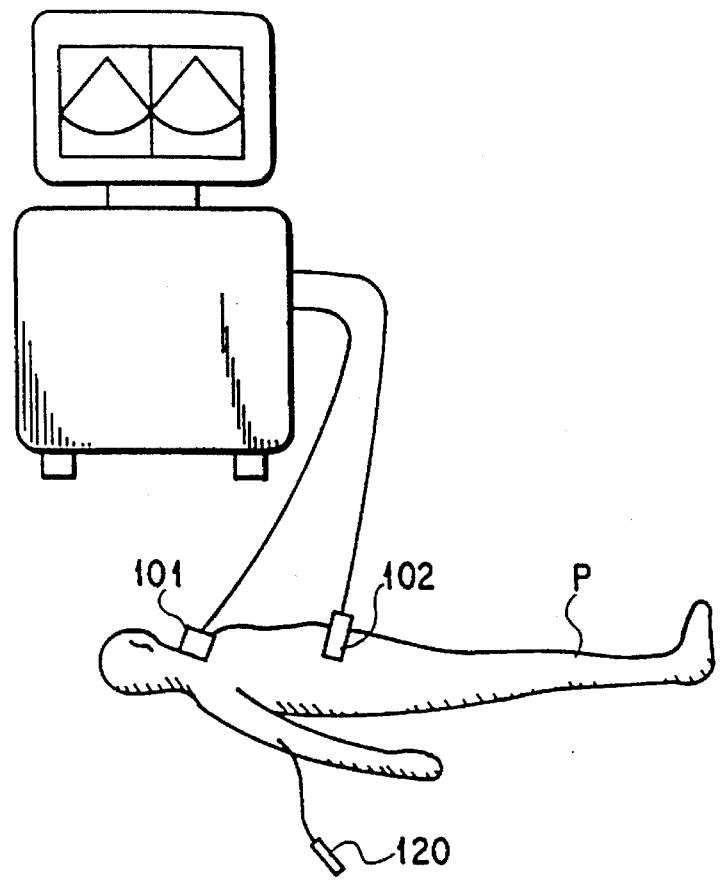
FIG. 23 is a view showing the state of attachment of two probes on an object to be examined.

In the arrangement shown in FIG. 22, a single transmission/reception circuit 114 is connected to at least two probes 101 and 102 via a switch (MUX) 113, so that the probes 101 and 102 can be selectively connected to the transmission/reception circuit 114. The output of the transmission/reception circuit 114 is connected to a parallel circuit of a B-mode processing system 115 and a CFM processing system 116. The outputs from the B-mode processing system 115 and the CFM processing system 116 are displayed on a monitor 118 via a single display system 117. Upon switching operation of the switch 113, the probes 101 and 102 are time-divisionally and selectively driven by the transmission/reception circuit 114 in units of frames or rasters.

when such an apparatus is used in practice, one probe 101 is set at a position of, e.g., the carotid artery, and the other probe 102 is set at a position separated from the probe 101, e.g., at the position of the portal vein, as shown in FIG. 23.

Figure 24:
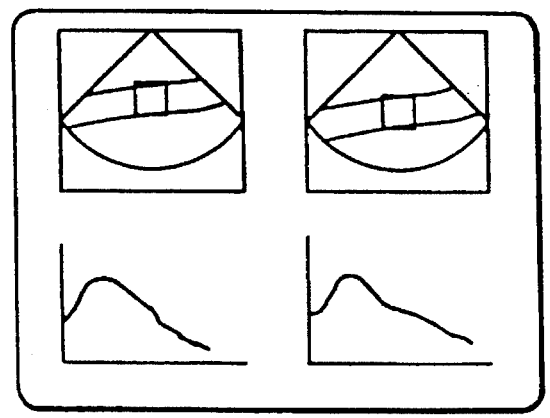
FIG. 24 is a view showing a display screen.

After a contrast medium is injected from a contrast medium injection device 120 into a patient P, the two probes 101 and 102 are driven synchronously or time-divisionally in units of frames or rasters to perform transmission/reception, so that the respective images can be simultaneously displayed without being influenced by ultrasonic waves transmitted from the other probes, i.e., while preventing beat noise components from being generated in images, as shown in FIG. 24.

In the arrangement shown in FIG. 22, since the two probes 101 and 102 are driven by the single transmission/reception circuit 114, and a B-mode image or a CFM image is obtained by the single processing system, the standard signal level can be prevented from varying due to a difference in, e.g., the gain characteristics of preamplifiers, and the like, and hence, comparison between two images can be executed under the same conditions.

As described above, according to the present invention, an ultrasonic diagnosis apparatus, which can prevent a contrast medium component of a reception signal from being saturated beyond the upper limit of the dynamic range, can be provided.

Also, according to the present invention, an ultrasonic diagnosis apparatus, which can provide various kinds of information such as a change, over time, in flow-in/out amount of a contrast medium in/from a region of interest in real time, can be provided.

Furthermore, according to the present invention, an ultrasonic diagnosis apparatus, which allows acquisition of images of two separate portions in real time while suppressing generation of beat noise components due to the influence of other ultrasonic waves, can be provided.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by said transmission/reception unit to obtain an ultrasonic image having a predetermined dynamic range;

a conversion unit for converting the ultrasonic image having the predetermined dynamic range obtained by said signal processing unit into an ultrasonic image having a dynamic range different from the predetermined dynamic range, said conversion unit including a plurality of log compressors having different log compression characteristics and selection means for selecting one of said plurality of log compressors to be used for log-compressing the ultrasonic image having the predetermined dynamic range obtained by said signal processing unit; and a display unit for displaying the ultrasonic image obtained by said conversion unit.

2. An apparatus according to claim 1, wherein said conversion unit comprises means for converting an ultrasonic image having the predetermined dynamic range obtained from the object to be examined in which a contrast medium is injected into an ultrasonic image having a dynamic range corresponding to a dynamic range of said display unit.

3. An apparatus according to claim 1, wherein said conversion unit comprises:

storage means for storing a plurality of different log compression curves;

read-out means for reading out one log compression curve from said storage means; and calculation means for executing calculation processing of the ultrasonic image having the predetermined dynamic range obtained by said signal processing unit on the basis of the one log compression curve read out by said read-out means so as to obtain an ultrasonic image having a specific dynamic range defined by the one log compression curve read out by said read-out means.

4. An apparatus according to claim 3, wherein one of the plurality of log compression curves has log compression characteristics corresponding to an ultrasonic reception signal from the object to be examined to which a contrast medium is injected.

5. An apparatus according to claim 4, wherein the log compression curve having log compression characteristics corresponding to the ultrasonic reception signal from the object to be examined in which the contrast medium is injected is set to have a larger rate of change in output signal with respect to a change in input signal value in a portion where an input signal is larger than other log compression curves.

6. An apparatus according to claim 3, further comprising:

contrast medium mode setting means, and wherein when said contrast medium mode setting means is set, said read-out means selects the log compression curve corresponding to the reception signal from the object to be examined to which the contrast medium is injected.

7. An apparatus according to claim 1, wherein one of said plurality of log compressors has log compression characteristics corresponding to an ultrasonic reception signal from the object to be examined in which a contrast medium is injected.

8. An apparatus according to claim 1, further comprising:

contrast medium mode setting means, and wherein when said contrast medium mode setting means is set, said selection means selects the log compressor corresponding to an ultrasonic reception signal from the object to be examined in which a contrast medium is injected.

9. An apparatus according to claim 1, further comprising:

setting means for setting a region of interest in the ultrasonic image obtained by said conversion unit; and calculation means for calculating a temporal change curve, to be displayed by said display unit, of image data in the region of interest set by said setting means.

10. An apparatus according to claim 9, wherein said temporal change curves are time-density curves.

11. An apparatus according to claim 1, further comprising:

setting means for setting a region of interest in the ultrasonic image obtained by said signal processing unit; and calculation means for calculating a temporal change curve, to be displayed by said display unit, of image data in the region of interest set by said setting means.

12. An apparatus according to claim 11, wherein said temporal change curves are time-density curves.

13. An apparatus according to claim 1, wherein said signal processing unit comprises means for obtaining at least one of a B-mode image, a Doppler image, and a color flow mapping image.

14. An apparatus according to claim 1, wherein the ultrasonic image is a color ultrasonic image obtained by color-processing predetermined ultrasonic parameters.

15. An ultrasonic diagnosis apparatus comprising:

a plurality of ultrasonic probes used for performing transmission/reception of ultrasonic waves for different portions of an object to be examined;

a single transmission/reception unit for driving said plurality of ultrasonic probes to perform transmission/reception so as to obtain ultrasonic images in units of frames each constituted by a plurality of scanning lines;

a switch unit for time-divisionally switching combinations of connections between each of said plurality of ultrasonic probes and said transmission/reception unit;

a setting unit for setting a region of interest in the ultrasonic images in units of frames;

a calculation unit for substantially simultaneously calculating a plurality of temporal change curves of image data in the regions of interest, set by said setting unit, of the ultrasonic images in units of frames; and a display unit for simultaneously displaying temporal change curves calculated by said calculation unit.

16. An apparatus according to claim 15, wherein said switch unit comprises means for time-divisionally switching combinations of connections between each of said plurality of ultrasonic probes and said transmission/reception unit in units of frames.

17. An apparatus according to claim 15, wherein said switch unit comprises means for time-divisionally switching combinations of connections between each of said plurality of ultrasonic probes and said transmission/reception unit in units of scanning lines.

18. An apparatus according to claim 15, wherein each of said plurality of ultrasonic probes comprises an integrated ultrasonic transducer unit.

19. An apparatus according to claim 15, wherein said signal processing unit comprises means for obtaining at least one of a B-mode image, a Doppler image, and a color flow mapping image.

20. An apparatus according to claim 15, wherein the ultrasonic image is a color ultrasonic image obtained by color-processing predetermined ultrasonic parameters.

21. An apparatus according to claim 15, wherein said temporal change curves are time-density curves.

22. An ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by said transmission/reception unit to obtain an ultrasonic image;

setting means for setting a plurality of regions of interest in the ultrasonic image obtained by said signal processing unit;

means for substantially simultaneously calculating a plurality of time-density curves of image data in the plurality of regions of interest set by said setting means; and a display unit for simultaneously displaying the ultrasonic image obtained by said signal processing unit and the plurality of time-density curves obtained by said curve calculating means.

23. An apparatus according to claim 22, further comprising:

means for calculating information representing a relationship between the plurality of time-density curves, and supplying the calculated information to said display unit.

24. An apparatus according to claim 23, wherein said time-density curves are temporal change curves.

25. An apparatus according to claim 22, wherein said signal processing unit comprises means for obtaining at least one of a B-mode image, a Doppler image, and a color flow mapping image.

26. An apparatus according to claim 22, wherein the ultrasonic image is a color ultrasonic image obtained by color-processing predetermined ultrasonic parameters.

27. An apparatus according to claim 22, wherein said time-density curves are temporal change curves.

28. An ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by said transmission/reception unit to obtain ultrasonic images in units of frames;

a setting unit for setting regions of interest in the ultrasonic images in units of frames obtained by said signal processing unit;

a filtering unit for filtering the regions of interest in units of frames set by said setting means;

a calculation unit for calculating a temporal change curve of image data in the regions of interest on the basis of image data in the regions of interest in units of frames filtered by said filtering unit; and a display unit for displaying the temporal change curve calculated by said calculation unit.

29. An apparatus according to claim 28, wherein said filtering unit comprises means for subtracting an initial value of a region of interest of one frame from the regions of interest in units of frames.

30. An apparatus according to claim 28, wherein said filtering unit comprises low-pass filter means.

31. An apparatus according to claim 28, wherein said signal processing unit comprises means for obtaining at least one of a B-mode image, a Doppler image, and a color flow mapping image.

32. An apparatus according to claim 28, wherein the ultrasonic image is a color ultrasonic image obtained by color-processing predetermined ultrasonic parameters.

33. An apparatus according to claim 28, wherein said temporal change curves are time-density curves.

34. An ultrasonic diagnosis apparatus comprising:

a transmission/reception unit for transmitting/receiving ultrasonic waves to/from an object to be examined to obtain an ultrasonic reception signal;

a signal processing unit for executing signal processing of the ultrasonic reception signal obtained by said transmission/reception unit to obtain an ultrasonic image having a predetermined dynamic range;

a conversion unit for converting the ultrasonic image having the predetermined dynamic range obtained by said signal processing unit into an ultrasonic image having a dynamic range different a display unit for displaying the ultrasonic image obtained by said conversion unit, wherein said conversion unit comprises means for converting an ultrasonic image having the predetermined dynamic range obtained from the object to be examined in which a contrast medium is injected into an ultrasonic image having a dynamic range corresponding to a dynamic range of said display unit.

35. An apparatus according to claim 34, wherein said conversion unit comprises:

a plurality of log compressors having different log compression characteristics; and selection means for selecting one of said plurality of log compressors to be used for log-compressing the ultrasonic image having the predetermined dynamic range obtained by said signal processing unit.

36. An apparatus according to claim 35, wherein one of said plurality of log compressors has log compression characteristics corresponding to an ultrasonic reception signal from the object to be examined in which a contrast medium is injected.

37. An apparatus according to claim 35, further comprising:

contrast medium mode setting means, and wherein when said contrast medium mode setting means is set, said selection means selects the log compressor corresponding to an ultrasonic reception signal from the object to be examined in which a contrast medium is injected.

38. An apparatus according to claim 34, further comprising:

setting means for setting a region of interest in the ultrasonic image obtained by said conversion unit; and calculation means for calculating a temporal change curve, to be displayed by said display unit, of image data in the region of interest set by said setting means.

39. An apparatus according to claim 38, wherein said temporal change curves are time-density curves.

40. An apparatus according to claim 34, further comprising:

setting means for setting a region of interest in the ultrasonic image obtained by said signal processing unit; and calculation means for calculating a temporal change curve, to be displayed by said display unit, of image data in the region of interest set by said setting means.

41. An apparatus according to claim 40, wherein said temporal change curves are time-density curves.

42. An apparatus according to claim 34, wherein said signal processing unit comprises means for obtaining at least one of a B-mode image, a Doppler image, and a color flow mapping image.

43. An apparatus according to claim 34, wherein the ultrasonic image is a color ultrasonic image obtained by color-processing predetermined ultrasonic parameters.

* * * * *